US008486690B2

(12) United States Patent
Burns

(10) Patent No.: US 8,486,690 B2
(45) Date of Patent: Jul. 16, 2013

(54) METHOD TO DETERMINE STATE OF A CELL EXCHANGING METABOLITES WITH A FLUID MEDIUM BY ANALYZING THE METABOLITES IN THE FLUID MEDIUM

(75) Inventor: David Hugh Burns, Montreal (CA)

(73) Assignee: McGill University, Montréal, QC (CA)

( * ) Notice: Subject to any disclaimer, the term of this patent is extended or adjusted under 35 U.S.C. 154(b) by 0 days.

(21) Appl. No.: 13/157,508

(22) Filed: Jun. 10, 2011

(65) Prior Publication Data

US 2011/0236922 A1   Sep. 29, 2011

Related U.S. Application Data

(63) Continuation of application No. 11/468,702, filed on Aug. 30, 2006, now Pat. No. 7,981,399.

(60) Provisional application No. 60/757,242, filed on Jan. 9, 2006, provisional application No. 60/654,497, filed on Feb. 25, 2005.

(51) Int. Cl.
*C12M 1/36* (2006.01)

(52) U.S. Cl.
USPC ............... 435/286.5; 435/286.6; 435/290.4

(58) Field of Classification Search
None
See application file for complete search history.

(56) References Cited

U.S. PATENT DOCUMENTS

| | | | |
|---|---|---|---|
| 5,541,081 A | 7/1996 | Hardy et al. | |
| 5,912,179 A | 6/1999 | Alvarez et al. | |
| 6,489,135 B1 | 12/2002 | Parrott | |
| 6,618,138 B2 | 9/2003 | Khoury | |
| 6,683,455 B2 | 1/2004 | Ebbels et al. | |
| 6,690,958 B1 | 2/2004 | Walker et al. | |
| 6,873,914 B2 | 3/2005 | Winfield et al. | |
| 7,005,255 B2 | 2/2006 | Kaddurah-Daouk et al. | |
| 7,191,068 B2 | 3/2007 | Rosenfeld et al. | |
| 7,202,395 B2 | 4/2007 | Leese et al. | |
| 2002/0188424 A1 | 12/2002 | Hoffman et al. | |
| 2003/0014420 A1 | 1/2003 | Jessee et al. | |
| 2003/0023386 A1 | 1/2003 | Aranibar et al. | |
| 2003/0030637 A1 | 2/2003 | Grinstein et al. | |
| 2003/0134304 A1 | 7/2003 | van der Greef et al. | |
| 2003/0137649 A1 | 7/2003 | Riordan et al. | |
| 2003/0229451 A1 | 12/2003 | Hamilton et al. | |
| 2004/0002842 A1 | 1/2004 | Woessner et al. | |
| 2004/0018500 A1 | 1/2004 | Glassbrook et al. | |
| 2004/0018501 A1 | 1/2004 | Allen et al. | |
| 2004/0019429 A1 | 1/2004 | Coffin et al. | |
| 2004/0019430 A1 | 1/2004 | Hurban et al. | |
| 2004/0019435 A1 | 1/2004 | Winfield et al. | |
| 2004/0023295 A1 | 2/2004 | Hamilton et al. | |
| 2004/0024293 A1 | 2/2004 | Lawrence et al. | |
| 2004/0024543 A1 | 2/2004 | Zhang et al. | |
| 2004/0033975 A1 | 2/2004 | Fu et al. | |
| 2004/0072143 A1 | 4/2004 | Timmis et al. | |
| 2004/0096930 A1 * | 5/2004 | Lendl et al. ............... 435/29 |
| 2004/0133355 A1 | 7/2004 | Schneider et al. | |
| 2004/0143461 A1 | 7/2004 | Watkins et al. | |
| 2004/0224301 A1 | 11/2004 | Toland et al. | |
| 2004/0268446 A1 | 12/2004 | Penttila et al. | |
| 2005/0014132 A1 | 1/2005 | Kaddurah-Daouk et al. | |
| 2005/0143928 A1 | 6/2005 | Moser et al. | |
| 2005/0154535 A1 | 7/2005 | Sun et al. | |
| 2005/0170372 A1 | 8/2005 | Afeyan et al. | |
| 2005/0239040 A1 | 10/2005 | Lindenberg | |
| 2005/0273275 A1 | 12/2005 | Afeyan et al. | |
| 2005/0283320 A1 | 12/2005 | Afeyan et al. | |
| 2006/0160065 A1 | 7/2006 | Timmis et al. | |
| 2007/0026389 A1 | 2/2007 | Kaddurah-Daouk et al. | |
| 2007/0032969 A1 | 2/2007 | Barrett et al. | |
| 2007/0043518 A1 | 2/2007 | Nicholson et al. | |
| 2007/0054347 A1 | 3/2007 | Rosendahl et al. | |
| 2007/0172820 A1 | 7/2007 | Kaddurah-Daouk et al. | |
| 2007/0254309 A1 | 11/2007 | O'Neill et al. | |

FOREIGN PATENT DOCUMENTS

| | | |
|---|---|---|
| EP | 1248852 | 10/2002 |
| WO | 9916895 | 4/1999 |
| WO | 9963057 | 9/1999 |
| WO | 0132802 | 5/2001 |
| WO | 0153518 | 7/2001 |
| WO | 02087132 | 10/2002 |
| WO | WO 02/099384 | * 12/2002 |
| WO | 2005033895 | 4/2005 |
| WO | 2005052575 | 6/2005 |
| WO | 2006086731 | 8/2006 |

(Continued)

OTHER PUBLICATIONS

Milki et al., Two-blastocyst transfer has similar pregnancy rates and a decreased multiple gestation rate compared with three-blastocyst transfer, Fertility and Sterility, 1999, 225-228, vol. 72, No. 2, American Society for Reproductive Medicine, Elsevier Science Inc.

Hunt et al., HLA and Fertility, HLA and the maternal-fetal Relationship, 1996, 134-156, R.G. Landes Company.

Zhaoqu, Y and Chun, D. "Research on Surface Enhanced Raman Spectrum (SERS) and Polarization Fluorescence Spectrum (PFS) of the Serum-free Cell Culture Solution.", Journal of Harbin University of C.E. & Architecture, 1997, 30 (1): 107-108.

The Second Office Action for Application No. 200680050781.9, dated Jan. 26, 2011, from the State Intellectual Property Office of the People's Republic of China (English translation; see p. 6 for a discussion of Zhaoqi and Chun, supra).

Agarwal et al., "Role of oxidative stress in female reproduction", Reproductive Biology and Endocrinology, 2005, 1-21, vol. 3, No. 28.

(Continued)

*Primary Examiner* — Jim Ketter
(74) *Attorney, Agent, or Firm* — Bereskin & Parr LLP/S.E.N.C.R.L., s.r.l.; Stephen Beney

(57) ABSTRACT

The present invention relates to a method for determining the ideal time for and outcome of reproductive health procedures including in vitro fertilization by establishing a correlation between the successful outcome of said procedure and the spectra of a body fluid obtained using a chosen analytical modality for a population of patients, acquiring for a patient a spectrum of the body fluid of the patient using said chosen modality.

10 Claims, 7 Drawing Sheets

FOREIGN PATENT DOCUMENTS

| WO | 2007035613 | 3/2007 |
|---|---|---|
| WO | 2007085851 | 8/2007 |
| WO | 2007109659 | 9/2007 |

OTHER PUBLICATIONS

Agarwal, "Assessing oxidative stress levels in semen using spectroscopy-based metabolic profiling: implications in male infertility", Urology News, 2006-2007, 44, vol. 15.
Bedaiwy et al., "Differential growth of human embryos in vitro: role of reactive oxygen species", Fertility and Sterility, 2004, 593-600, vol. 82, No. 3.
Brison et al., "Identification of viable embryos in IVF by non-invasive measurement of amino acid turnover", Human Reproduction, 2004 2319-2324, vol. 19, No. 10.
Brison, "Predicting human embryo viability: the road to non-invasive analysis of the secretome using metabolic footprinting", Reproductive Biomedicine Online, 2007, 296-302, vol. 15, No. 3.
Deepinder et al., "Role of metabolomic analysis of biomarkers in the management of male infertility", Expert Rev. Mol. Diagn., 2007, 351-358, vol. 7, No. 4.
Dunn et al., "Metabolics: Current analytical platforms and methodologies", Trends in Analytical Chemistry, 2005, 285-294, vol. 24, No. 4.
Goodacre et al., "Metabolomics by numbers: acquiring and understanding global metabolic data", Trends in Biotechnology, 2004, 245-252, vol. 22, No. 5.
Goodacre, "Understanding complex biological systems with metabolomics: an overview", Abstract and Presentation at Workshop entitled "Application of proteomics and transcriptomics in EMF Research", Helsinki, 2005.
Houghton et al., "Non-invasive amino acid turnover predicts human embryos developmental capacity", Human Reproduction, 2002, 999-1005, vol. 17, No. 4.
Lopes et al., "Quantification of embryo quality by respirometry", Theriogenology, 2007, 21-31, vol. 67.
Macas, "Metabolic status of oocyte and IVF success—is there a relationship?", Journal fur Fertilitat und Reproduktion, 2006, 16-18, vol. 16, No. 4.
Riley et al., "Simultaneous measurement of 19 components in serum-containing animal cell culture media by fourier transform near-infrared spectroscopy", Biotechnology progress, 2001, 376-378, vol. 17, No. 2.
Sakkas et al., "Noninvasive methods to assess embryo quality", Curr. Opin. Obstet. Gynecol., 2005, 283-288, vol. 17.
Scott et al., "Noninvasive metabolomic profiling of human embryo culture media using Raman spectroscopy predicts embryonic reproductive potential: a prospective blinded pilot study", Fertility and Sterility, 2008, 77-83, vol. 90, No. 1.
Seli et al., "Noninvasive metabolomic profiling of embryo culture media using Raman and near-infrared spectroscopy correlates with reproductive potential of embryos in women undergoing in vitro fertilization", Fertility and Sterility, 2007, 1350-1357, vol. 88, No. 5.
Singh et al., "Metabolomics: Approaches to assessing oocyte and embryo quality", Theriogenology, 2007, S56-S62, vol. 68.
Thomas et al., "Fourier transform infrared spectroscopy of follicular fluids from large and small antral follicles", Human Reproduction, 2000, 1667-1671, vol. 15, No. 8.
Vergouw et al., "Metabolomic profiling by near infrared spectroscopy as a tool to assess embryo viability: a novel, non-invasive method for embryo selection", Human Reproduction, 2008, 1499-1504, vol. 23, No. 7.
International Search Report and Written Opinion for PCT/IB2006/002389 dated Aug. 13, 2008.
International Search Report and Written Opinion for PCT/IB06/02366 dated Nov. 10, 2008.
Weckwerth et al., "Metabolomics: from pattern recognition to biological interpretation", Drug Discovery Today, 2005, 1551-1558, vol. 10, No. 22.
Armand et al., "Simultaneous measurement of erythrocyte ATP, ADP, AMP and 2,3-DPG by tandem mass spectrometry", Blood, Nov. 16, 2001, vol. 102, No. 11, p. 562A.
Averna et al., "A decrease in 1H nuclear magnetic resonance spectroscopically determined citrate in human seminal fluid accompanies the development of prostate adenocarcinoma", J Urol., Feb. 2005, 173(2):433-8.
Hamamah et al., "Quantification by magnetic resonance spectroscopy of metabolites in seminal plasma able to differentiate different forms of azoospermia", Hum Reprod., Jan. 1998; 13(1):132-5.
Sjostrand, M., "IL-5 release by enriched human bone marrow CD34+ cells", Journal of Allergy and Clinical Immunology, Mosby, Inc. US, Feb. 1, 2003, vol. 111, No. 1, p. S115.
European Supplemental Search Report for European Patent Application No. 06795387.7 dated Mar. 30, 2010.
European Search Opinion for European Patent Application No. 06795387.7 dated Apr. 12, 2010.
Agarwal A., Prabakaran S.A., "Mechanism, measurement, and prevention of oxidative stress in male reproductive physiology", Indian J Exp Biol., Nov. 2005; 43(11): 963-974.
Gardner and Sakkas, "Mouse embryo cleavage, metabolism and viability: role of medium composition", Hum Reprod., Feb. 1993; 8(2): 288-295.
Gerard N., Loiseau S., Duchamp G. and Seguin F., "Analysis of the variations of follicular fluid composition during follicular growth and maturation in the mare using Proton nuclear magnetic resonance", Reproduction 124, 241-248 (2002).
Lane M. and Gardner D.K., "Selection of viable mouse blastocysts prior to transfer using a metabolic criterion", Human Reproduction, vol. 11, No. 9, pp. 1975-1978, 1996.
Leese H.J., "Metabolic control during preimplantation mammalian development", Hum Reprod Update, Jan. 1995,; 1(1): 63-72, Review.
Segalen J., De Certaines J.D., Le Calve M., Colleu D., Bansard J.Y. and Rio M., "1H nuclear magnetic resonance of human seminal plasma in in vitro fertilization attempts: use of automatic spectrum analysis", J Reprod Fertil., Jan. 1995; 103(1): 181-7.
Tomlins A.M., Foxall P.J., Lynch M.J., Parkinson J., Everett J.R., Nicholson J.K., "High resolution 1H NMR spectroscopic studies on dynamic biochemical processes in incubated human seminal fluid samples", Biochim Biophys Acta., Mar. 2, 1998; 1379(3): 367-380.
Ludwig et al., "Experience with the elective transfer of two embryos under the conditions of the German embryo protection law: results of a retrospective data analysis of 2573 transfer cycles", Human Reproduction, 2000, 319-324, vol. 15, No. 2, European Society of Human Reproduction and Embryology.
Gributs et al., "Haar transform analysis of photon time-of-flight measurements for quantification of optical properties in scattering media", Applied Optics, 2003, 2923-2910, vol. 42, No. 16, Optical Society of America.
Fuzzi et al., "HLA-G expression in early embryos is a fundamental prerequisite for the obtainment of pregnancy", Eur. J. Immunol., 2002, 311-315, 32, Wiley-VCH Verlag GmbH, Weinheim.
McMaster et al., "HLA-G isoforms produced by placenta cytotrophoblasts and found in amniotic fluid are due to unusual glycosylation", The Journal of Immunology, 1998, 5922-5928, 160, The American Association of Immunologists.
McShane et al., "Improving complex near-IR calibrations using a new wavelength selection algorithm", Applied Spectroscopy, 1999, 1575-1581, vol. 53, No. 12, Society for Applied Spectroscopy.
Menicucci et al., "Non-classic sHLA class I in human oocyte culture medium", Human Immunology, 1999, 1054-1057, 60, American Society for Histocompatibility and Immunogenetics, Elsevier Science Inc.
Sies, "Oxidative stress II", Oxidants and Antioxidants, 1991, Academic Press, London.
Hailiwell et al., "Free radicals in biology and medicine", 1999, 1632-1636, 3ed., Oxford: Oxford University Press Inc.
Almagor et al., "Pregnancy rates after communal growth of preimplantation human embryos in vitro", Fertility and Sterility, 1996, 394-397, vol. 66, No. 3, American Society for Reproductive Medicine.
Gianaroli et al., Preimplantation genetic diagnosis increases the implantation rate in human in vitro fertilization by avoiding the transfer of chromosomally abnormal embryos, Fertility and Science, 1997, 1128-1131, vol. 68, No. 6, American Society of Reproductive Medicine, Elsevier Science Inc.

Abu-Zidan et al., "Proteolysis in severe sepsis in related to oxidation of plasma protein", Eur. J. Surg., 2002, 119-123, 168, Taylor & Francis.
Balaban et al., "The effect of pronuclear morphology on embryo quality parameters and blastocyst transfer outcome", Human Reproduction, 2001, 2357-2361, vol. 16, No. 11, European Society of Human Reproduction and Embryology.
Le Bouteiller et al., "The functionality of HLA-G is emerging", Immunological Reviews, 1999, 233-244, vol. 167, Munksgaard, Denmark.
Fish et al., "The graduated Embryo Score (GES) predicts blastocyst formation and pregnancy rate from cleavage-stage embryos", Human Reproduction, 2001, 1970-1975, vol. 16, No. 9, European Society of Human Reproduction and Embryology.
Rijnders et al., "The predictive value of day 3 embryo morphology regarding blastocyst formation, pregnancy and implantation rate after day 5 transfer following in-vitro fertilization or intracytoplasmic sperm injection", Human Reproduction, 1998, 2869-2873, vol. 13, No. 10, European Society of Human Reproduction and Embryology.
Scott et al., "The successful use of pronuclear embryo transfers the day following oocyte retrieval", Human Reproduction, 1998, 1003-1013, vol. 13, No. 4, European Society of Human Reproduction and Embryology.
Zollner et al., "The use of a detailed zygote score after IVF/ICSI to obtain good quality blastocysts: the German experience", Human Reproduction, 2002, 1327-1333, vol. 17, No. 5, European Society of Human Reproduction and Embryology.
Fenwick et al., "Time from insemination to first cleavage predicts development competence of human preimplantation embryos in vitro", Human Reproduction, 2002, 407-412, vol. 17, No. 2, European Society of Human Reproduction and Embryology.
Spyropoulou et al., "A prospective randomized study comparing the outcome of in-vitro fertilization and embryo transfer following culture of human embryos individually or in groups before embryo transfer on day 2", Human Reproduction, 1999, 76-79, vol. 14, No. 1, European Society of Human Reproduction and Embryology.
Levron et al., "A prospective randomized study comparing day 3 with blastocyst-stage embryo transfer", Fertility and Sterility, 2002, 1300-1301, vol. 77, No. 6, American Society for Reproductive Medicine, Elsevier Science Inc.
Milki et al., "Accuracy of day 3 criteria for selecting the best embryos", Fertility and Sterility, 2002, 1191-1195, vol. 77, No. 6, American Society for Reproductive medicine, Elsevier Science Inc.
Albuszies et al., "Antioxicant therapy in sepsis", Intensive Care Med, 2003, 1632-1636, 29, Springer-Verlag.
Magli et al., "Chromosome mosaicism in day 3 aneuploid embryos that develop to morphologically normal blastocysts in vitro", Human Reproduction, 2000, 1781-1786, vol. 15, No. 8, European Society of Human Reproduction and Embryology.
Alikani et al., "Cleavage anomalies in early human embryos and survival after prolonged culture in-vitro", Human Reproduction, 2000, 2634-2643, vol. 15, No. 12, European Society of Human Reproduction and Embryology.

Blake et al., "Cleavage stage versus blastocyst stage embryo transfer in assisted conception", The Cochrane Library, 2007, 1-80, Issue 1, Wiley & Sons Ltd.
Tsai et al., "Clinical value of early cleavage embryo", International Journal of Gynecology & Obstetrics, 2002, 293-297, 76, International Federation of Gynecology and Obstetrics, Elsevier Science Ireland ltd.
Fournel et al., "Comparative reactivity of different HLA-G monoclonal antibodies to soluble HLA-G molecules", Tissue Antigens, 2000, 510-518, 55, Denmark.
Milki et al., "Comparison of blastocyst transfer with day 3 embryo transfer in similar patient populations", Fertility and Sterility, 2000, 126-129, vol. 73, No. 1, American Society for Reproductive Medicine, Elsevier Science inc., USA.
Gardner et al., "Culture and transfer of human blastocysts increases implantation rates and reduces the need for multiple embryo transfers", Fertility and Sterility, 1998, 84-88, vol. 69, No. 1, American Society for Reproductive Medicine, Elsevier Science Inc., US.
Bos-Mikich et al., "Early cleavage of human embryos: an efffective method for predicting successful IVF/ICSI outcome", Human Reproduction, 2001, 2658-2661, vol. 16, No. 12, European Society of Human Reproduction and Embryology.
Shoukir et al., "Early cleavage of in-vitro fertilized human embryos to the 2-cell stage: a novel indicator of embryo quality and viability", Human Reproduction, 1997, 1531-1536, vol. 12, No. 7, European Society of Human Reproduction and Embryology.
Lundin et al., "Early embryo cleavage is a strong indicator of embryo quality in human IVF", Human Reproduction, 2001, 2652-2657, vol. 16, No. 12, European Society of Human Reproduction and Embryology.
Lonergan et al., "Effect of time interval from insemination to first cleavage on the developmental characteristics, sex ratio and pregnancy rate after transfer of bovine embryos", Journal of Reproduction and Fertility, 1999, 159-167, 117, Journals of Reproduction and Fertility Ltd.
Ziebe et al., "Embryo morphology or cleavage stage: how to select the best embryos for transfer after in-vitro fertilization", Human Reproduction, 1997, 1545-1549, vol. 12, No. 7, European Society for Human Reproduction and Embryology.
Puissant et al., "Embryo scoring as a prognostic tool in IVF treatment", Human Reproduction, 1987, 705-708, vol. 2, No. 8, IRL Press Limited, Oxford, England.
Tesarik et al., "Embryos with high implantation potential after intracytoplasmic sperm injection can be recognized by a simple, non-invasive examination of pronuclear morphology", Human Reproduction, 2000, 1396-1399, vol. 15, No. 6, European Society of Human Reproduction and Embryology.
Van Lierop et al., "Detection of HLA-G by specific sandwich ELISA using monoclonal antibodies G233 and 56B", Molecular Human Reproduction, 2002, 776-784, vol. 8, No. 8, European Society of Human Reproduction and Embryology.
Office Action for Japanese Patent Application No. 2008-549939 dated Apr. 19, 2012 from the Japanese Patent Office (English Translation).

* cited by examiner

METHOD TO DETERMINE STATE OF A CELL EXCHANGING METABOLITES WITH A FLUID MEDIUM BY ANALYZING THE METABOLITES IN THE FLUID MEDIUM

CROSS REFERENCE TO RELATED APPLICATIONS

This application is a continuation of application Ser. No. 11/468,702, filed Aug. 30, 2006 which claims the benefit of Provisional Application No. 60/757,242, filed Jan. 9, 2006, and the entire contents of which are hereby incorporated by reference.

TECHNICAL FIELD

The present invention relates to determining a state of a cell exchanging metabolites with a fluid medium by analyzing the metabolites in the fluid medium, and to uses thereof.

BACKGROUND OF THE INVENTION

Metabolomics

With the completion of the sequencing of the human genome, it has become apparent that genetic information alone is incapable of providing a comprehensive characterization of the biochemical and cellular functioning of complex biological systems. As a result, the focus of much molecular biological research is shifting toward proteomics and metabolomics, broadly defined as the systematic analysis of proteins and small molecules such as polypeptides, hormones and neurotransmitters (and their metabolites) in a physiological environment such as a biological sample, a cell, tissue, or organism. Because proteins and metabolites are far more numerous, diverse, and fragile than genes, existing tools for their discovery, identification, and quantification do not meet the needs of researchers or clinicians.

One important aspect of proteomics is the identification of proteins with inherent mutations or altered expression levels. Differences in protein and metabolite levels over time or among populations can be correlated with disease states, drug regimens, or alterations to metabolism. Identified molecular species may serve as biological markers (biomarkers) for the disease or condition in question, thereby permitting new methods of diagnosis, prognosis and disease management to be developed or more suitably tailored for the patient. In order to discover such biological markers, it is helpful to obtain accurate measurements of relative differences in protein and metabolite levels between different sample types, a process referred to as differential phenotyping.

In vitro Fertilization (IVF) Treatment

The field of assisted reproductive technologies (ART) including IVF, whether applied to humans or animals, is a somewhat inexact science or art. The ability to assess viability of spermatozoa (sperm cells), oocytes (eggs) and embryos is done essentially by visual appearance under a microscope. Visual appearance of these cells does not correlate well with viability in many cases. No other information about what is going on in the cells is available to ART specialists to guide the process. The whole procedure is performed with the hope that viable gametes will be selected and that these gametes will produce viable embryos that will successfully implant in a uterus and go on to produce healthy offspring. While genetic testing of embryos by extracting one cell is possible to determine at least some factors of viability, such an "invasive" procedure can adversely affect the embryo. No technique presently exists that allows embryologists and other ART specialists to efficiently assess the viability of these cells for ART procedures.

IVF has proven to be the most viable alternative available to infertile couples and is increasingly becoming recognized as appropriate "first line" procedure over other treatment options.

IVF procedures can be broken down into six broad procedural stages: 1) stimulation of the female using fertility hormone drugs to produce a large cohort population of oocytes; 2) retrieval of oocytes; 3) male gamete collection and preparation, followed by fertilization of the egg; 4) culturing of resulting zygotes/embryos in growth media; 5) embryo selection, and finally 6) embryo transfer. Typically, the key events comprising embryo implantation and pregnancy are not considered part of the IVF process since they are outside the control of the procedure per se. In current IVF practice, oocytes and embryos that are selected for the procedure are assumed to be viable or healthy, based primarily on subjective morphological criteria and development patterns (in the case of the embryo); no biological metrics are available to assist in this very critical selection process. Unused embryos are typically cryopreserved.

ART services now make it possible to offer treatment options also to patients who a priori are not infertile, but who wish to push back or control the "biological clock to enhance and/or preserve their reproductive function (or fertility) (fertility preservation). The application of ART services to otherwise normal, fertile population has created a new therapeutic paradigm of Fertility Preservation. The need for controlled fertility delay may be further appreciated for example if a patient is undergoing chemotherapy wherein reproductive function may be perturbed.

Today there are no practical biological criteria or analytical methods enabling selection of oocyte, sperm, or embryo to ensure efficacy or safety of the IVF procedure. Consequently, with no analytical methodologies available to reliably assess oocyte competency at the front end of the IVF procedure, embryologists have resorted to subjective and non-standardized embryo development criteria and morphology as indicators of embryo quality and, by inference, original oocyte quality.

SUMMARY OF THE INVENTION

A novel technology platform has been identified based on the confluence of two scientific disciplines: (1) biospectroscopy, the application of different forms of spectroscopic analysis in human biology that can be used to identify, quantify and validate proteomic and molecular diagnostic biomarkers; and (2) metabolomics, the science that examines and integrates the dynamic interplay between multiple small molecule biomarkers in a biological sample (both in fluids and in solid tissue) to understand complex biological processes and functions. Metabolomics can be employed to investigate changes in metabolic profiles in tissues and/or cell types.

The term biospectroscopy-based metabolomics (BSM) is used here to describe this technology platform. The BSM platform is used herein to analyze a sample's proteomic and molecular biomarker makeup, which then converts the data into a unique "metabolomic profile" using informatics. Each profile translates into a unique "fingerprint" or "signature" that defines the metabolic status of the target sample and, thus, the patient from whom the sample is derived. "Metabolomic profiling" may be employed to systematically distinguish between the oftensubtle differences that separate normal physiology from the onset or progression of disease, or an individual's response to pharmacotherapy.

Thus, without limiting the scope of the invention, it can be appreciated that BSM has broad application to human and animal health. Such broad application of the BSM technology platform includes but is not limited to: (1) non-invasive, molecular diagnostic and prognostic assessment as in for example, Alzheimer's Disease (AD), monitoring fetal-maternal health and in vitro fertilization methodologies, and (2) pharmacodiagnostics-based strategies for drug discovery and development using metabolomic profiling to identify surrogate markers of efficacy and safety. These applications employ biomarker-based metabolomic profiling using the focused application engendered in BSM technology.

Various forms of biospectroscopic analysis have been shown to be useful for non-invasive, in-vivo monitoring of several tissues, organs and fluids. In vitro analysis of solid tissue, individual cells and biological fluids is also performed using this methodology. Biospectroscopy has many advantages, including simplicity, accuracy and specificity, ease of use, rapid analysis, low-cost instrumentation, simultaneous measurement of multiple analytes in a single specimen, and the advantage of continuous, real-time monitoring by either point-of-care or remote analysis. Using the BSM platform, one can now perform high speed, sophisticated metabolomic analysis in less than one minute with liquid samples as small as 20 microliters, using a small device.

Metabolomics is a valuable extension of a growing understanding of the interplay of genes and proteins. The medical and scientific communities are now realizing that genomics, transcriptomics and proteomics are just a small part of homeostasis. While the genome is representative of what might be, and the proteome defines what has been expressed, it is the metabolome that represents the real-time functional status of the cell, tissue, organ or individual with respect to health and disease. The cumulative effects of all the "downstream events" of expressed proteins and protein modifications are represented in a pool of small molecules that reflect the cell's functional status. Profiling this molecular inventory (the metabolome) provides a correlate of a cell's health, disease, aging and the effects of drugs and xenobiotics in its environment. Thus, the ability to capture this information offers technological advancement to molecular diagnostics, prognostics and drug discovery across several scientific disciplines. It offers the practitioner invaluable decision making capability in multiple clinical settings.

The scope of reproductive health includes normal reproductive function as well as reproductive failure and infertility. Metabolomic profiling of biomarkers in the field of reproductive health, and more particularly in assisted reproductive technologies (ART) has not been explored. It has been discovered that biomarker profiling may be used to reliably to identify viable, biologically competent oocytes, sperm, and embryos in order to enhance treatment outcomes (pregnancy) in in vitro fertilization (IVF) procedures as well as reduce the risk of multiple births by allowing judicious pre-selection of fewer, but only viable, embryos for transfer.

Thus, it would be a significant contribution to the art to provide a method for determining the metabolomic profile of a sample useful for determining, for example, the viability of an oocyte, sperm or embryo, and hence the probability of success of any further in vitro fertilization procedures and related methods by optically measuring body fluids and gamete or embryo culture media used in related IVF laboratory procedures.

It would be highly desirable to be provided with a method to determine state of a cell exchanging metabolites with a fluid medium by analyzing the metabolites in the fluid medium. The cells may be cells growing in a suitable culture medium, such as an embryo or stem cells. The cells may be those of the uterine wall and the fluid medium may be the endometrial fluid.

The present invention provides a method to determine state of a cell exchanging metabolites with a fluid medium by analyzing the metabolites in the fluid medium.

The present invention also provides a system and method for determining the metabolomic profile of a sample useful for determining, for example, the probability of success of in vitro fertilization procedures and related methods by optically measuring body fluids and gamete or embryo culture media used in related IVF laboratory procedures.

Also provided is a method and apparatus for correlating spectra, such as single wavelength including fluorescence, multi-wavelength optical absorption, Raman scattering spectra, or magnetic resonance spectra of metabolites in fluids, such as body fluids, gamete or embryo culture media, wherein such spectra with state of at least one cell, including a gamete or a plurality of cells in an embryo.

In some embodiments, there is provided an assisted reproductive technology (ART) method. This method combines growing in vitro at least one embryo in a culture medium, analytically testing the culture medium of the at least one embryo at intervals during growth of the embryo to determine state of the embryo, and using the state of the embryo to determine at least one of:
  a time to transfer the embryo into a uterus;
  a time to subject the embryo to short term storage for future transfer into a uterus;
  a time to subject the embryo to cryopreservation for future transfer into a uterus;
  an adjustment to the culture medium to continue growing of the embryo; and
  a time to transfer the embryo into a different culture medium to continue growing of the embryo.

In some embodiments, this method further comprises determining a viability of the oocyte, the spermatozoa and the uterus by analytically testing a respective follicular fluid, seminal plasma and uterine lining fluid, wherein the single embryo is transferred when the viability of the oocyte, the spermatozoa, the uterus indicates a good probability of implantation or pregnancy for transfer of the embryo.

The embryo can be obtained by in vitro fertilizing at least one oocyte using spermatozoa.

In some embodiment, the adjustment to the culture medium is repeatedly determined as the embryo grows.

In conventional IVF, no reliable information about viability of an embryo is available, and so transfer is sometimes delayed since an embryo that survives to day 3, 4 or 5 is likely to be more viable. However, it is desirable to transfer an embryo known to be (or having an indication of a good probability to be) viable as early as possible. The viability state of the embryo may increase as the embryo develops up to a certain point of maturity, such as day 2, however, in some embryos, the viability may not increase significantly more as the embryo matures in vitro. Therefore, in some embodiments, the time to transfer the embryo is determined as the earliest time at which the embryo reaches a good probability threshold for implantation.

It will be appreciated that the present invention can be applied, without limitation, to mammals, for example to humans, bovines, equines, felines, canines, caprines, and cetaceans.

When a number of the oocytes are fertilized and a number of the embryos are grown, the embryos can be selected for transfer using at least the determined state.

The analytically testing may comprise obtaining a spectrum of the culture medium. In some embodiments, the spectrum is calibrated determining an effective correlation between recorded spectrum of the culture medium of a number of embryos and recorded success of pregnancy using the number of embryos, and the state is determined from performing the correlation on the spectrum. In some embodiments, the spectrum is an optical spectrum. The spectrum may contain information related to oxidative stress components of the culture medium.

When the embryo is cryopreserved, a spectrum of the cryopreserved culture medium may be periodically obtained and the state can be determined from the cryopreserved culture medium optical spectrum to monitor the cryopreserved embryo during cryopreservation.

In some embodiments, there is provided an assisted reproductive technology (ART) method. This method comprises extracting a plurality of oocytes in their own follicular fluid, analytically testing the follicular fluid of each one of the oocytes to determine a state of the oocyte, and selecting the oocytes using the state for one of cryopreservation and fertilization. The analytical testing of follicular fluid is essentially the same as for a culture medium.

In some embodiments, there is provided a method of generating probability data for the successful outcome of a reproductive health procedure in a patient. This method comprises acquiring for at least one cell exchanging metabolites with a fluid medium, chosen from an oocyte, a spermatozoid, and an embryo, a spectrum of at least one metabolite in the fluid medium using a chosen analytical modality, and generating probability data for the at least one cell using the acquired spectrum and an established correlation between the successful outcome of a reproductive health procedure and the spectra of a metabolite in a fluid medium obtained using the chosen analytical modality for a population of patients. The analytical testing of these fluid media is essentially the same.

The analytical modality may be single or multiwavelength optical absorption, Raman scattering or optical fluorescence. The optical spectrum may be within the short wavelength near infrared range. The chosen analytical modality may also be NMR.

The reproductive health procedure may relate to pre-eclampsia, IAI or intra-amniotic inflammation, pre-term labor/birth, recurrent miscarriage/abortion, embryo implantation, sex determination, environmental contamination/infection, ectopic pregnancy, normal pregnancy or to endometriosis.

In other embodiments, the invention provides an assisted reproductive technology (ART) method. This method comprises providing a sample of one or more spermatozoa in seminal plasma, analytically testing the plasma of the spermatozoa to determine a state of the spermatozoa, and selecting the spermatozoa using the state for one of cryopreservation and fertilization.

In other embodiments, the invention provides an assisted reproductive technology (ART) method. This method comprises analytically testing the endometrial fluid of a uterus of a patient to determine a viability of the uterus for implantation of an embryo, and determining a time of implantation using the viability. For example, if the viability is weak, the testing is repeated, and the time of implantation is determined when the viability is stronger. For example, at least one of dietary, rest/exercise, and medicinal intervention can be provided to the patient to improve the viability.

The endometrial fluid can be measured optically in situ, and the analytically testing then involves obtaining an optical spectrum.

In some embodiments, there is provided a method to determine state of a cell exchanging metabolites with a fluid medium. This method combines acquiring for at least one cell a spectrum of at least one metabolite in the fluid medium using a chosen analytical modality, and generating probability data for the at least one cell using the acquired spectrum and an established correlation between the state of at least one cell and the spectra of a metabolite in a fluid medium obtained using the chosen analytical modality for a population of cells.

In some embodiments, the analytical modality is optical spectroscopy, such as optical Raman scattering, optical absorption or optical fluorescence. In some embodiments, the optical spectrum provides information about oxidative stress of the fluid medium.

In other embodiments, there is provided a method for sustaining or growing one or more cells in a culture medium. This method comprises adjusting the culture medium using a state of the cells determined from a spectrum of the culture medium obtained using a chosen analytical modality.

In some embodiments of the invention, there is provided an apparatus for controlling culture of one or more cells growing in vitro in a culture medium. This apparatus combines a spectral acquisition device for acquiring a spectrum of the culture medium, a database of correlation data relating spectral data to a state of the cells, a state determination processor generating data representing the state using the correlation data and the spectrum, a culture medium controller generating control signals for effecting an adjustment in the culture medium in response to the data representing the state. The controller can be fully automated and thus control valves and switches for changing culture medium parameters, or it can provide a report for a technician to make the required adjustment. In some embodiments, the spectrum contains information regarding oxidative stress of at least one component of the culture medium.

As an example, the adjustment to the culture medium can be in ambient temperature or gas composition, such as dissolved oxygen. Likewise, the adjustment can be an addition of a substance to the culture medium, for example to change pH or add protein. In other cases, it is appropriate that the adjustment be a substitution of the culture medium.

The apparatus can operate to make culture medium changes using the state as feedback. The time for an adjustment to yield a measurable change in the state will typically determine the feedback loop cycle time. Of course, when an adjustment immediately affects the culture media's spectrum, the spectrum is reacquired following the adjustment, and then the change in the state as determined immediately following the adjustment and at some subsequent time is used to assess whether the adjustment was beneficial to the sustaining or growing of the cells.

For the purpose of the present invention the following terms are defined below.

The term "body fluid" is intended to mean whole blood, blood plasma, blood serum, urine, saliva, tear fluid, amniotic fluid, cerebrospinal fluid (CSF), breast milk, vaginal fluid, uteral fluid, seminal fluid.

The term "culture media" is intended to mean any mixture of nutrients and salt solutions that can be used to sustain viable cells in in vitro culture in the laboratory, including gametes and embryos. With some analytical modalities, such as optical spectroscopy, the culture media can be frozen without affecting the ability to obtain useful spectra.

The term "patient" is intended to mean a subject to be investigated, observed, monitored or studied, whether human or animal.

The term "non-invasive" is intended to include transdermal or transcutaneous spectroscopy, that is performed in situ, or in-vivo in a patient, and minimally invasive, such as by withdrawing a small volume of body fluid.

The term "oxidative stress related disease" is intended to mean a condition that either causes oxidative stress or is caused by or dependent on oxidative stress.

The term "oxidative stress component" is intended to mean the disturbance in the pro-oxidant/antioxidant balance of a biochemical component of body fluid culture media or other sample under investigation, in favor of the former, leading to possible tissue damage. Likewise "oxidative stress components" is intended to mean such disturbance in the pro-oxidant/antioxidant balance of a plurality of biochemical components of the body fluid culture media or other sample under investigation in favor of the former, leading to possible tissue damage. The term "redox signature" is intended to mean an aggregate of oxidative stress components or OS biological byproducts derived from multi-wavelength optical absorption spectroscopy or NMR spectroscopy.

The term "antibody" refers to a polypeptide substantially encoded by an immunoglobulin gene or immunoglobulin genes, or fragments thereof. The recognized immunoglobulin genes include the kappa, lambda, alpha, gamma, delta, epsilon and mu constant region genes, as well as myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively.

The term "biomarkers" or "target biomarkers" refer to the profile of proteins, enzymes, peptides, small molecules, oxidative stress compounds, or other biological compounds that are associated with the specific procedure or medical condition or disease being studied, such as in vitro fertilization or Alzheimer's disease. The data relating to a specific biomarker makeup is converted into a novel "metabolomic profile" or "fingerprint". Each profile is typically analyzed using proprietary informatics that correlates the data to a clinical condition or outcome. Metabolomic profiling is used to systematically distinguish between the often subtle differences between normal physiology and the onset or progression of disease, or an individual's response to a therapeutic compound. This technology is applicable across several scientific disciplines and fields of use.

The term "embryo quality" is defined as a quality indicative of embryos being competent for use in subsequent procedures, and reflect embryo viability, for use in procedures involving embryo selection and transfer, such as in vitro fertilization, and implantation to achieve a pregnancy, and short-term storage, and long term storage, including cryopreservation. Short term storage may be defined as storage of from about 3 days to about 5 years. Long term storage may be further defined as storage for longer than about 5 years to storage for an indefinite period of time.

The term "oocyte quality" is defined as a quality indicative of oocytes being competent for use in subsequent procedures, and reflect oocyte viability, for use in procedures involving oocyte selection and transfer, such as in vitro fertilization, and implantation to achieve a pregnancy, and short-term storage, and long term storage, including cryopreservation. Short term storage may be defined as storage of from about 3 days to about 5 years. Long term storage may be further defined as storage for longer than about 5 years to storage for an indefinite period of time.

The term "sperm quality" is defined as a quality indicative of sperm being competent for use in subsequent procedures, and reflect sperm viability, for use in procedures involving sperm selection and transfer, such as in vitro fertilization, and implantation to achieve a pregnancy, and short-term storage, and long term storage, including cryopreservation. Short term storage may be defined as storage of from about 3 days to about 5 years. Long term storage may be further defined as storage for longer than about 5 years to storage for an indefinite period of time.

The term "HLA-G" refers to human leukocyte antigen G and unless otherwise stated includes both the soluble and insoluble forms. The term may in appropriate context refer to either the antigen or the genetic locus.

The terms "integrins, ubiquitin, selectins, growth factors, inhibitins and other hormones, other enzymes, small molecules and peptides are typical biomarkers which have their various recognized scientific meanings.

The term "immunoassay" is an analysis or methodology that utilizes an antibody to specifically bind an analyte. The immunoassay is characterized by the use of specific binding properties of at least one particular antibody to isolate, target, or quantify the analyte.

The terms "isolated", "purified", or "biologically pure" refer to material which is substantially or essentially free from components which normally accompany it as found in its native state.

The term "label" is used in reference to a composition detectable by spectroscopic, photochemical, biochemical, immunochemical, or chemical means. For example, useful labels include fluorescent dyes, electron-dense reagents, calorimetric, enzymes, for example, as commonly used in ELISA, biotin, dioxigenin, or haptens and proteins for which antisera or monoclonal antibodies are available can be made detectable.

All references referred herein are hereby incorporated by reference.

BRIEF DESCRIPTION OF THE DRAWINGS

Further features and advantages of the present invention will become apparent from the following detailed description, taken in combination with the appended drawings, in which.

It will be noted that throughout the appended drawings, like features are identified by like reference numerals.

DETAILED DESCRIPTION OF THE PREFERRED EMBODIMENTS

Figure 1:
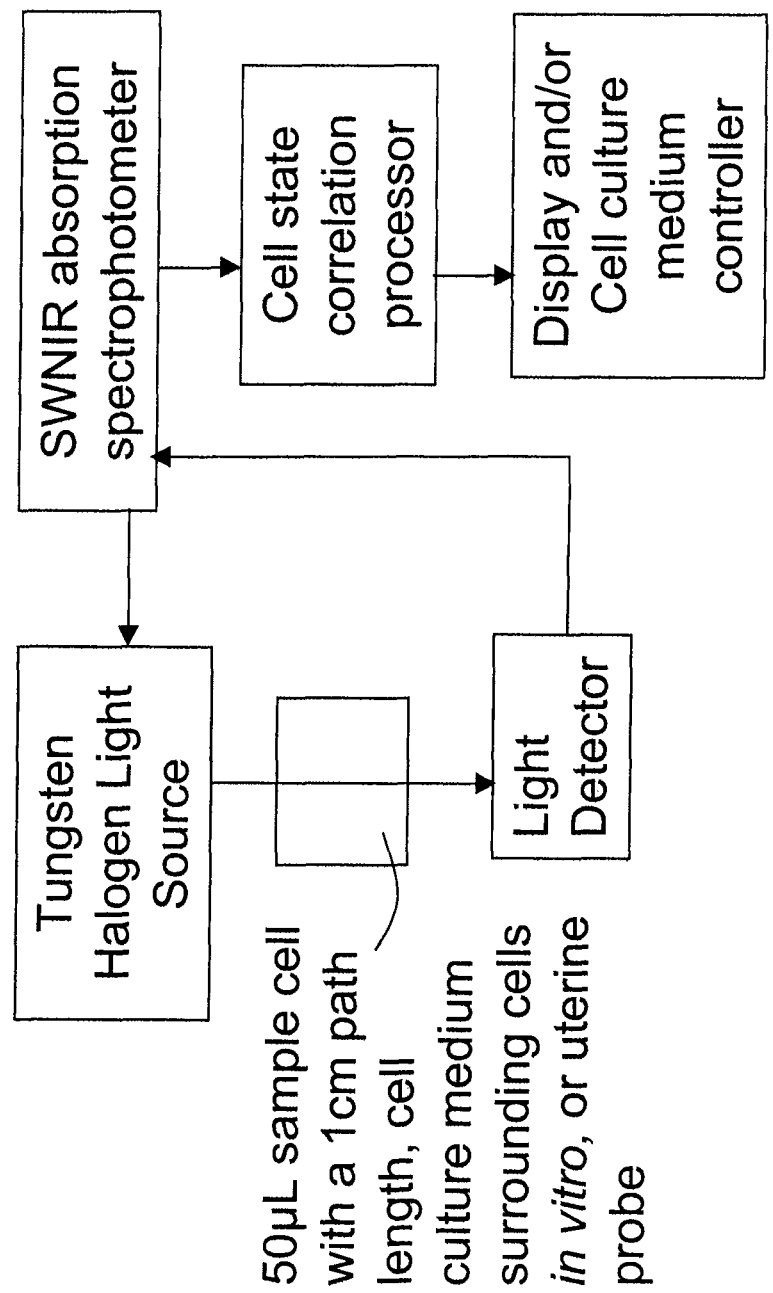
FIG. 1 is a schematic drawing of an optical oxidative stress measurement device having a 50 μL sample cell with a 1 cm path length supplied with light from a broadband Tungsten Halogen lamp via a first optical fiber, a short wavelength near infrared (SWNIR) spectrophotometer coupled to an opposite end of the sample cell via a second optical fiber for detecting CW intensity in the 600 nm to 1100 nm range, and a computer connected to the spectrophotometer for recording and analyzing the spectra.

The present invention provides a method and apparatus for correlating spectra, such as multi-wavelength optical absorption, Raman scattering spectra, or magnetic resonance spectra of culture media or body fluids, such as body fluids from a patient with an oxidative stress dependent disease.

Oxidative stress measurement has not been employed in a clinical environment as a tool in diagnosing or predicting the onset of a condition. The present invention provides a tool that allows rapid measurement of oxidative stress suitable for use in clinical setting.

Oxidative stress longitudinally (over time) has not been measured previously with a view to better study the time course of a condition thereby be able to intervene and correct the level of oxidative stress. The present invention provides a device that is able to measure oxidative stress quickly and non-invasively in a manner suitable for use with any patients.

As an example, the instant invention provides a tool to measure one or more oxidative stress components in body fluid using optical analysis. The body fluid analyzed according to the invention may be any one of, or a combination of, whole blood, blood plasma, blood serum, urine, saliva, tear fluid and cerebrospinal fluid (CSF), amniotic fluid, breast milk, vaginal or uteral fluid. Another aspect of the instant invention provides a tool to measure one or more oxidative stress components in a culture medium to determine oocyte quality, embryo quality, sperm quality etc. The optical analysis may be achieved with wavelengths from optical spectra in a variety of ranges, such as the NIR, SWNIR, and THz ranges. In addition to absorption spectra, Raman spectra and fluorescence spectra may also be analyzed.

Also provided are a method and apparatus to determine probability data of the presence of an oxidative stress dependent condition in a patient or in a sample. A correlation is established between an oxidative stress dependent disease and spectra of a body fluid obtained using a chosen analytical modality for a population of patients or samples. For the patient whose probability data is to be determined, a spectrum of the body fluid is obtained using the chosen modality. The probability data for the patient is generated using the acquired spectrum and the established correlation.

The present invention also provides methods for determining the quality of embryos for use in subsequent procedures, which includes embryo viability. These methods include transfer of the embryo to the uterus with in vitro fertilization and embryo transfer (IVF/ET) and Tubal Embryo Transfer (TET), by assessing the metabolomic profiles of biomarkers of embryo viability.

The BSM technology platform may be applied to many different diagnostic, prognostic and monitoring indications, including In vitro Fertilization procedures (IVF). Studies have indicated that BSM can easily be performed in non-invasive manner and with a high degree of sensitivity and specificity. Small prototype devices may be readily adapted for large-scale production of commercial units.

Most methods directed to metabolomics rely on technologies such as mass spectrometry, NMR, HPLC, electrophoresis and a variety of analytical assays based on proteomics, including microarrays and immunoassays, and the like, as their core technologies. While these are useful approaches for some applications, such as in research, service or clinical reference laboratories, they are costly and complex. In contrast, BSM is performed using a small, easy to use and portable point-of-care device that can. even be used for screening purposes.

Relative quantitative information about components of chemical or biological samples can be obtained from spectra by normalizing the spectra to yield peak intensity values that accurately reflect concentrations of the responsible chemical species. A normalization factor is computed from peak intensities of those inherent components whose concentration remains constant across a series of samples. Relative concentrations of a component occurring in different samples can be estimated from the normalized peak intensities. Unlike conventional methods, internal standards or additional reagents are not required. The methods are particularly useful for differential phenotyping in proteomics and metabolomics research, in which molecules varying in concentration across samples are identified. These identified species may serve as biological markers for disease or response to therapy.

Free radicals are atoms or molecules that contain unpaired electrons in their outer orbitals. Their electronic configurations render these chemical species highly reactive with membrane lipids, proteins, nucleic acids and other cellular substrates. Free radicals may be derived from environmental sources or may be generated de novo within tissues. The superoxide anion ($0^{2-}$), hydrogen peroxide ($H_2O_2$), singlet oxygen, hypochlorous acid (HOCl), peroxynitrite (ONOO—) and the hydroxyl radical (OH*) are examples of cornon, endogenously-produced reactive oxygen species (ROS). Transition metals, such as ferrous iron ($Fe^{2+}$) or cuprous copper ($Cu^{1+}$), play a vital role in cellular redox chemistry by reducing $H_2O_2$ to the highly-cytotoxic OH* radical (Fenton catalysis). In mammalian tissues, evolutionarily-conserved antioxidant enzymes (e.g. the superoxide dismutases, catalase, the glutathione peroxidases and various reductases) operate in concert with a host of nonenzymatic, low-molecular-weight antioxidant compounds (e.g. GSH, thioredoxin. ascorbate, the tocopherols, uric acid, melatonin, bilirubin) to maintain redox homeostasis. By maintaining transition metals in a relatively low redox state, metalbinding proteins, such as ferritin, transferrin, lactoferrin, the metallothioneins and ceruloplasmin, contribute substantially to the antioxidant protection of tissues and body fluids.

Oxidative stress (0s) has been defined as "a disturbance in the pro-oxidant/antioxidant balance in favor of the former, leading to possible [tissue] damage". This balance can be related to one or more biochemical component of the body fluid. Oxidative stress has been implicated as a key common pathway for cellular dysfunction and death and a potential therapeutic target in a broad spectrum of human medical conditions including cancer, diabetes, obstructive lung disease, inflammatory bowel disease, cardiac ischemia, glomerulonephritis, macular degeneration and various neurodegenerative disorders.

It is thus known to measure oxidative stress in blood plasma and cerebrospinal fluid (CSF) using chromatographic techniques and mass spectrometry. Such analytical techniques are time consuming and typically involve obtaining a significant quantity of body fluid to obtain a measurement of oxidative stress.

The biological markers utilized in the subject invention, include inflammatory markers, oxidative stress markers, and cell damage markers, or combinations thereof. Inflammatory markers include, but are not limited to, cytokines or other inflammatory mediators that promote the attraction of white blood cells or inflammatory cells. Inflammatory markers can be, but are not necessarily, released from inflammatory cells. Inflammatory markers include, but are not limited to, 8-isoprostane, myeloperoxidase, IL-6, and C-reactive protein. Oxidative stress markers indicate cell damage caused by oxidants or free-radicals. Oxidative stress markers include the radicals and oxidants that reach their respective targets, such as lipids, protein, or DNA, as well as indirect markers of the damage caused by radicals and oxidants. Oxidative stress markers include, but are not limited to, free iron, 8-isoprostane, superoxide dismutase, glutathione peroxidase, lipid hydroperoxidase, dityrosine, and 8-hydroxyguanine. Cell damage markers include biological molecules (e.g., enzymes) wherein their release is associated with necrotic or damaged cells. Cell damage markers include, but are not limited to, creatine kinase and lactate dehydrogenase. Some biological markers can be classified as more than one type of marker. For example, 8-isoprostane can be classified as both an inflammatory marker and an oxidative stress marker.

The present invention provides a method for processing spectral data containing peaks having peak intensities. A set of spectra is obtained from a plurality of chemical samples such as biological samples containing metabolites, proteins or peptides. The spectra can be mass spectra obtained by, for example, electrospray ionization (EST), matrix-assisted laser desorption ionization (MALDI), or electron-impact ionization (EI). Peak intensities in each spectrum are scaled by a normalization factor to yield peak intensities that are proportional to the concentration of the responsible component. Based on scaled peak intensities, relative concentrations of a particular sample component can be estimated. The normalization factor is computed in dependence on chemical sample components whose concentrations are substantially constant in the chemical samples. In one embodiment, these components are not predetermined and are inherent components of the chemical samples. In another embodiment, the normalization factor is computed from ratios of peak intensities between two (e.g., first and second) spectra of the set and is a nonparametric measure of peak intensities such as a median.

Assisted Reproductive Technologies (ART) Including in vitro Fertilization

The methods of the current invention may be used to determine the successful timing of in vitro fertilization procedures.

Currently, in vitro fertility (IVF) laboratories are able to select pre-embryos only on the basis of their morphology and rate of in vitro cleavage during the first 48 to 72 hours after fertilization. These criteria are useful, but are not always good indicators of developmental potential. In most cases, 3 or 4 embryos are chosen based on these relatively crude indicators and then transferred into the uterine cavity. If additional, more stringent pre-embryo selection criteria were available, based on biochemical, genetic or developmental parameters, it would be possible to transfer one or two healthy pre-embryos, which have the highest chance of survival, without exposing patients to the psychological trauma caused by recurrent embryo implantation failure, spontaneous abortions, multiple IVF trials or the risk of multiple pregnancy. Therefore, there is a medical need for a more predictive test for successful implantation.

Reproductive Health (IVF). There are no commercially available diagnostic tests to assess oocyte, sperm, or embryo competency. Currently, embryos are selected based on an arbitrary morphology rating scale that is highly subjective. Preimplantation Genetic Diagnosis (PGD) is a procedure that tests for a limited number of genetic conditions but can not be used to predict embryo competency. PGD is a highly invasive, non-standardized procedure that is only available in a few specialized laboratories in the US. Further, it is expensive, time consuming and is highly controversial. There are simply no tests available to assess oocyte, sperm or embryo quality. Other applications of this technology in reproductive health and obstetrics include the assessment of: pre-eclampsia, IAI or intra-amniotic inflammation, pre-term laborhirth, recurrent miscarriage/abortion, implantation, sex determination, environmental contamination, infection, ectopic pregnancy, normal pregnancy, endometriosis, and the like.

The Oocyte

Until recently, it was assumed that oocytes were generally "normal" or competent. They were not viewed as a source of potential complication in IVF except in obvious cases where severe morphological variants were observed, or if the egg was immature (with the primary metric being size). In such cases, defective eggs were, and continue to be, discarded. However, mounting scientific evidence is changing this paradigm of thought as several new reports (most recently, the 2005 Annual meeting of ASRM) have demonstrated that between 50%. and as many as 75%, of all oocytes are abnormal (aneuploidic) in younger women (21-31 y/o), and this number increases dramatically with age. Generally speaking, there has been a paucity of research investigating human oocyte viability at any level, genomic, proteomic or metabolomic. As a result, there are no acceptable procedures for oocyte selection.

Genomics Testing

Some genomics testing techniques have only recently been adapted (<2 years) in attempt to assess oocyte competency (e.g., Comparative Genomic Hybridization). These techniques are in their infancy, they have not been standardized or validated, and are far from becoming practical, commonplace procedures in the IVF laboratory. Currently, these procedures are very expensive, labor intensive and highly invasive to the oocyte since a biopsy of the egg's polar bodies is required. The impact of such biopsies, if any, is unknown.

More recently, preimplantation Genetic Diagnosis (PGD) has been used to indirectly study oocyte quality by assessing the incidence of aneuploidy in otherwise healthy, morphologically competent embryos. In these studies, even oocytes from younger women were found to have a high incidence of chromosomal abnormalities; by inference, the abnormal embryos were derived from abnormal oocytes. Convincingly, the incidence of aneuploidy detected in oocytes is very similar using either CGH or PGD procedures and in the order of approximately 50%.

The Embryo

Historically, the embryo has received more attention as the target of intervention for monitoring and predicting IVF success. The "holy grail" of IVF is to know which embryos are viable, competent embryos and which ones are not. The hypothesis stands that if there was a procedure to consistently identify and select only high quality embryos—those with the greatest likelihood of producing a pregnancy—such embryos could be routinely selected for transfer. This, in turn, carries the expectation of improving pregnancy rates while reducing multiple births because fewer embryos would have to be transferred if they were known prospectively to be viable.

Morphological Assessment

Today, a morphological assessment of embryos, based on a +1 to +4 grading system, is the primary determinant of viability in the TVF laboratory. The embryos are typically evaluated using "Graduated Embryo Scoring (GES). The GES system evaluates embryos during the first 72 hours following fertilization. Each embryo is scored on a maximum of 100 points. Embryos with a GES score of >70 have the highest chance of developing into viable blastocysts that following embryo transfer (ET) will subsequently implant into the uterine lining (or endometrium) and produce a viable pregnancy. GES thus establishes a sound basis for advising patients with regard to selecting embryos for ET.

An embryo's developmental pattern during the culturing process (e.g., cleavage rate, fragmentation, inclusion bodies, inner cell mass, etc.) is also evaluated, but there is even less agreement among embryologists regarding the use of these metrics. Morphological assessment is burdened with obvious difficulty due to the lack of national or international standards. The inherent inter- and intra-observer variability associated with a subjective grading system, and the lack of any correlative biological metrics to anchor the process against. Moreover, the fundamental scientific flaw with this grading system is the axiom that morphological analysis cannot be accepted as a measure of biological functionality. The limitations of this process were again the subject to intense interest at the recent ASRM annual conference. Nevertheless, embryologists have had to rely on this grading system since no alternative methods have emerged.

By analyzing the metabolomic spectral profiles of the growing cells and embryos, adjustment for nutrients, supplements, pH and metabolites is assessed. This allows a continuous monitoring and optimization of the growth of cells and embryos. For example, the determination of level of oxidative stress can be measured and counteracted by the supplementation of chemical entities such as anti-oxidant. More specifically, a weaker embryo may be supplemented with more oxygen or the growth medium may be modified to improve viability of that embryo, such as modifying the medium pH, removing metabolites or supplementing the medium with nutrients, based on media monitoring. A weak embryo growing in a day-3 medium may be transfer to grow into a day-5 medium based on media monitoring of the present invention.

Uterine Assessment

The viability of the uterus for implantation of the embryo can be correlated with the analytical spectral components of the endometrial fluid, namely the fluid lining the wall of the uterus.

The methodology can be applied to determine the metabolomic profile of cervical mucous and endometrial of the uterus lining to determine biological receptivity of the endometrium to embryo implantation. Cervical mucous, as a biological fluid, can be analyzed by various spectroscopic methods to determine metabolomic profiles indicative of a receptive endometrium while the endometrial lining of the various uterus can be examined non-invasively by various spectroscopic methods employing fiber optics that can be inserted through the cervix directly into the uterus. Metabolomic determination of the endometrium will lead to increased embryo implantation rates and, hence, pregnancy.

Preimplantation Genetics Diagnosis and Genomics Testing

Genomics testing (i.e., CGR) of embryos is subject to the same limitations as noted above for the oocyte and, to date, embryo CGR has not received credible attention from the scientific community. However, the ART field currently benefits from the procedure of Preimplantation Genetic Diagnosis that can be used to screen developing embryos for a limited number of specific genetic diseases and aneuploidies that affect 9 of the possible 23 chromosome pairs. PGD is a labor intensive procedure used in combination with another procedure called fluorescence in situ hybridization (FISH). Unfortunately, PGD/FISH, lacks both sensitivity and specificity when it comes to identifying global oocytes and embryos viability for IVF. While PGD is useful in detecting aneuploidies that could impact embryo viability, it has not proven useful for the global assessment of embryo quality.

PGD is viewed as a controversial procedure since it requires a single cell biopsy of the early embryo and the health risks inherent in the process are unknown. While the biopsies are performed in the IVF lab, they must be sent to another remote genetics laboratory for chromosomal analysis. PDG is also regarded as an experimental procedure by FDA and ASRM, and bioethical questions have been raised due to the nature of the genetic information obtained from the test. PGD is also cost-prohibitive as a routine, mainstream test for IVF. Until very recently, the field's preoccupation with PGD has likely kept scientists from pursuing other genomic methodologies or proteomics and metabolomics.

Compared to metabolomic profiling of this invention, PGD is a very costly and invasive procedure upon the embryo and thus carries a high degree of unknown risk; limited to testing of genetic conditions; and is time consuming. Moreover, PGD has not proven to be a useful tool for determining embryo viability except in the genomic assessment of aneuploidy. Since it is a complex and expensive procedure, it is not likely to become a mainstream option for routine embryo assessment. For many scientific and sociopolitical reasons, PGD is still considered an experimental procedure. Accordingly, the introduction of metabolomic profiling as a test of global oocyte and embryo competency is a major advance in the art.

Embryo Biomarkers

At least one molecular biomarker of embryo viability has been examined with some rigor, a molecule called soluble human leukocyte antigen (sHLAG). This protein is measured by immunoassay and thus is more cumbersome, has a long turn-around time (hours), and is expensive to run. Due to volume limitations (of media samples), the assay cannot be run in duplicate so statistical accuracy is compromised. Other proteomic biomarkers (e.g., integrin beta, ubiquitin, HCG, others), have recently been postulated for the embryo; however, these markers have not been studied extensively and their role as indicators of embryo viability, if any, requires further investigation.

Enabling Single Embryo Transfer (SET)

Establishing confidence in a single embryo transfer process as a means to reduce multiple births, without compromising pregnancy rates, is the goal of IVF practitioners, ASRM and insurance providers alike. Unfortunately, this has proven to be an elusive goal so far. The availability of metabolomic profiling is expected to give the practitioner the choice of multiple embryo transfer or single embryo transfer in IVF clinical practice. Therefore the benefits of metabolomic testing can be appreciated and include: (i) enhanced treatment outcomes (i.e., pregnancy rate) and a concomitant reduction in the incidence of multiple births (triplets, or greater); (ii) a reduction in medical risk to mother and offspring; (iii) reduced medical costs associated with providing medical care for multiple premature infants; (iv) broader insurance coverage for IVF; (v) greater confidence for those seeking treatment for infertility.

Metabolomic profiling is also expected to enable the development of other benefits for the ART community including: 1) frozen donor egg banks that offer only prescreened, viable eggs for prospective recipients, and 2) "oocyte rescue" which is the collection of competent, extra-numeric eggs for cryopreservation followed by fertilization at a future date in a subsequent IVF cycle.

sHLAG Biomarker Assay

This single biomarker assay for sHLAG is currently being employed in IVF procedures. The kits additionally contain instructions for performing the methods of the current invention.

The present invention will be more readily understood by referring to the following examples which are given to illustrate the invention rather than to limit its scope.

Stem Cells

The invention can likewise be applied to determining the viability of one or more stem cells in a culture medium by analyzing the culture medium. In accordance with the present invention, an assessment of the growth medium of the stem cells to determine the oxidative stress of these stem cells is necessary to maximize the differentiation of stem cells into β-cells or into differentiated cell type. A differentiating factor may be identified with a monitoring spectrum of the stem cell growth medium, such as proteins and other metabolites.

Example 1

Measurement of OS from Short Wavelength Near Infrared (SWNIR) Spectroscopy of Blood Plasma Sampling Methodology Prior to analysis samples were thawed for one hour to reach room temperature and then centrifuged for 30 min. For cleaning and preconditioning, the sample cell was first rinsed with 200 μl of 0.1 M NaOH followed by 3×200 μl Millipore water.

Short Wavelength Near Infrared (SWMIR) Spectroscopy

A SWNIR spectrum was recorded of the third water rinse serving as a control. Thereupon, 75 μl of sample was injected into the sample cell and a sample spectrum recorded using the apparatus as shown in FIG. 1.

Short wavelength near infrared spectra were obtained from the prepared samples using the following protocol. For the measurements, an American Holographic near infrared spectrophotometer was used. The spectrophotometer is equipped with a two channel input port so that a reference could be obtained simultaneous with the measurement sample. Spectra acquired covered the 580 to 1100 nm region. Integration time of the detector was 100 milliseconds. All samples were measured 50 times and the results averaged to reduce spectral noise. Samples were introduced into a sample cell with 10 mm internal path length using an eppendorff pipette. Approximately 75 microliter sample was used. After spectral data were obtained, the sample cell was washed using 200 microliter—0.1 M NaOH followed by 3 volumes of 200 microliter Millipore water. After each sample a separate reference spectrum was taken of the third water rinse solution. This allowed monitoring of contamination of the sample cell or changes in alignment of the optical system. Each sample spectrum was referenced to the consecutive water sample for later processing.

IVF sampling. Oocyte: at the time of oocyte collection, an aliquot consisting of approximately 100 μl of normally discarded follicular fluid is retrieved from the Petri dish once the oocyte has been identified and removed to holding nutrient media.

Embryo: spent culture media, that is normally discarded, is collected at the end of each stage of IVF culture (from fertilization to cleavage to blastocyst) for analysis by BSM. Individual embryo culture is the preferred method of preparing embryos for this procedure but is not mandatory. Alternatively, discarded culture media from PGD, assisted hatching and other related ART procedures can also be analyzed in a like manner. The samples can be analyzed by BSM immediately or stored frozen for future analysis. Oocyte and embryo selection is determined based on the unique metabolomic profile of biomarkers in the respective samples.

Fluid samples may be frozen and used as such to obtain a spectrum or may be subsequently thawed prior to obtaining a spectrum.

Analysis Methodology

A Priori Wavelength Selection

Figure 2:
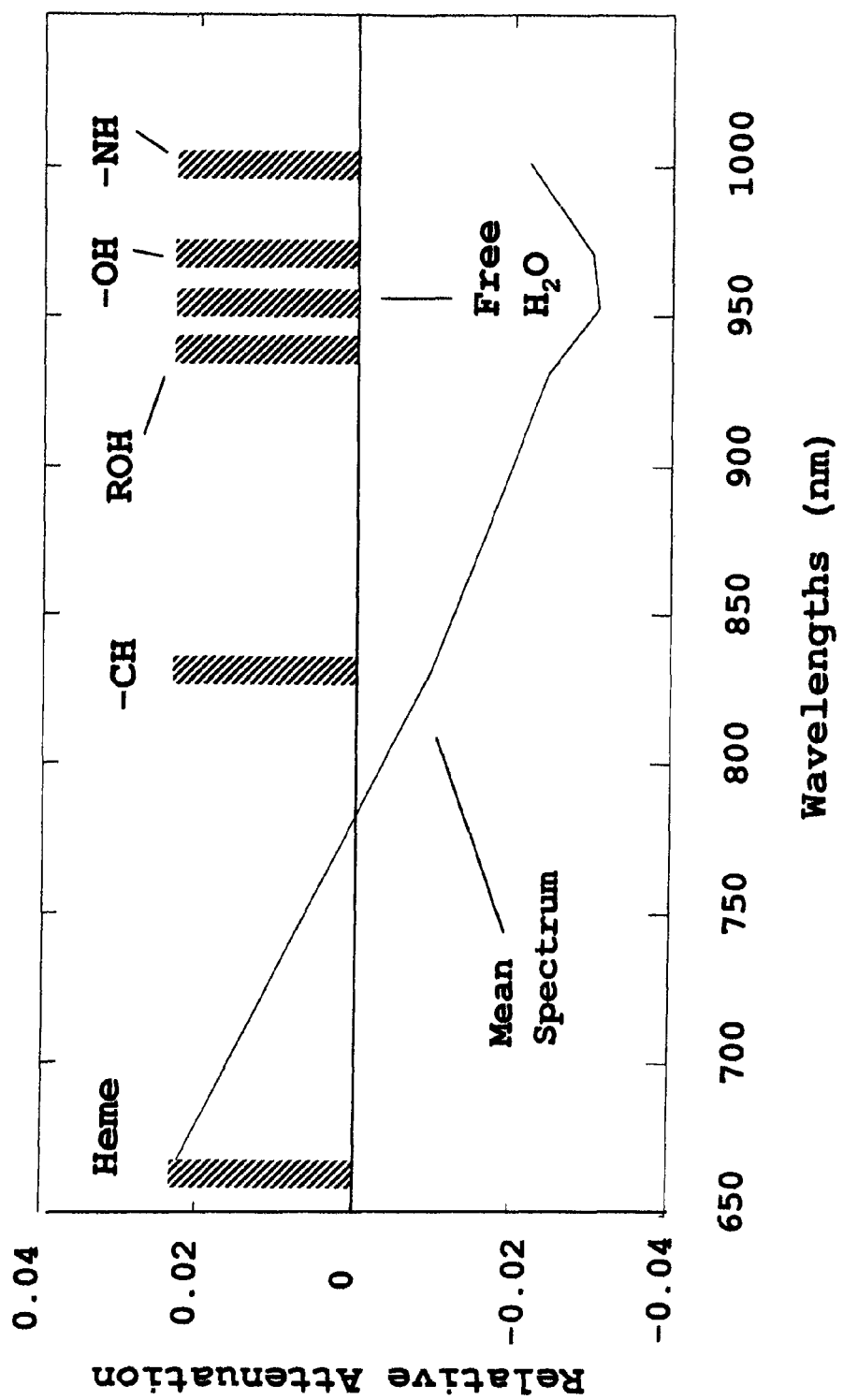
FIG. 2 is graph showing absorption levels from a variety of molecular species in the 600 to 1000 nm wavelength range.
Figure 3:
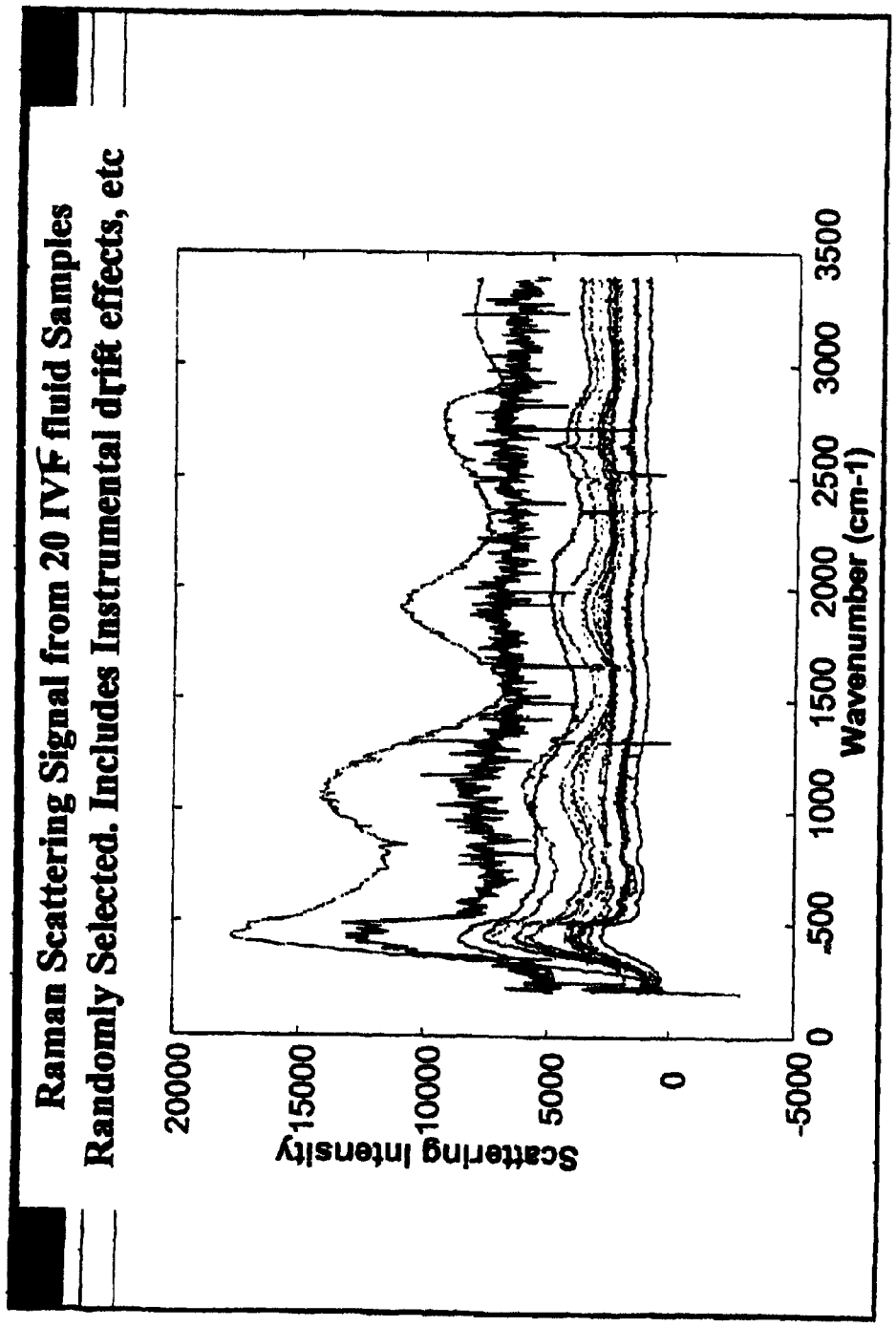
FIG. 3 shows a Raman spectra of 20 IVF embryo culture media samples.
Figure 4:
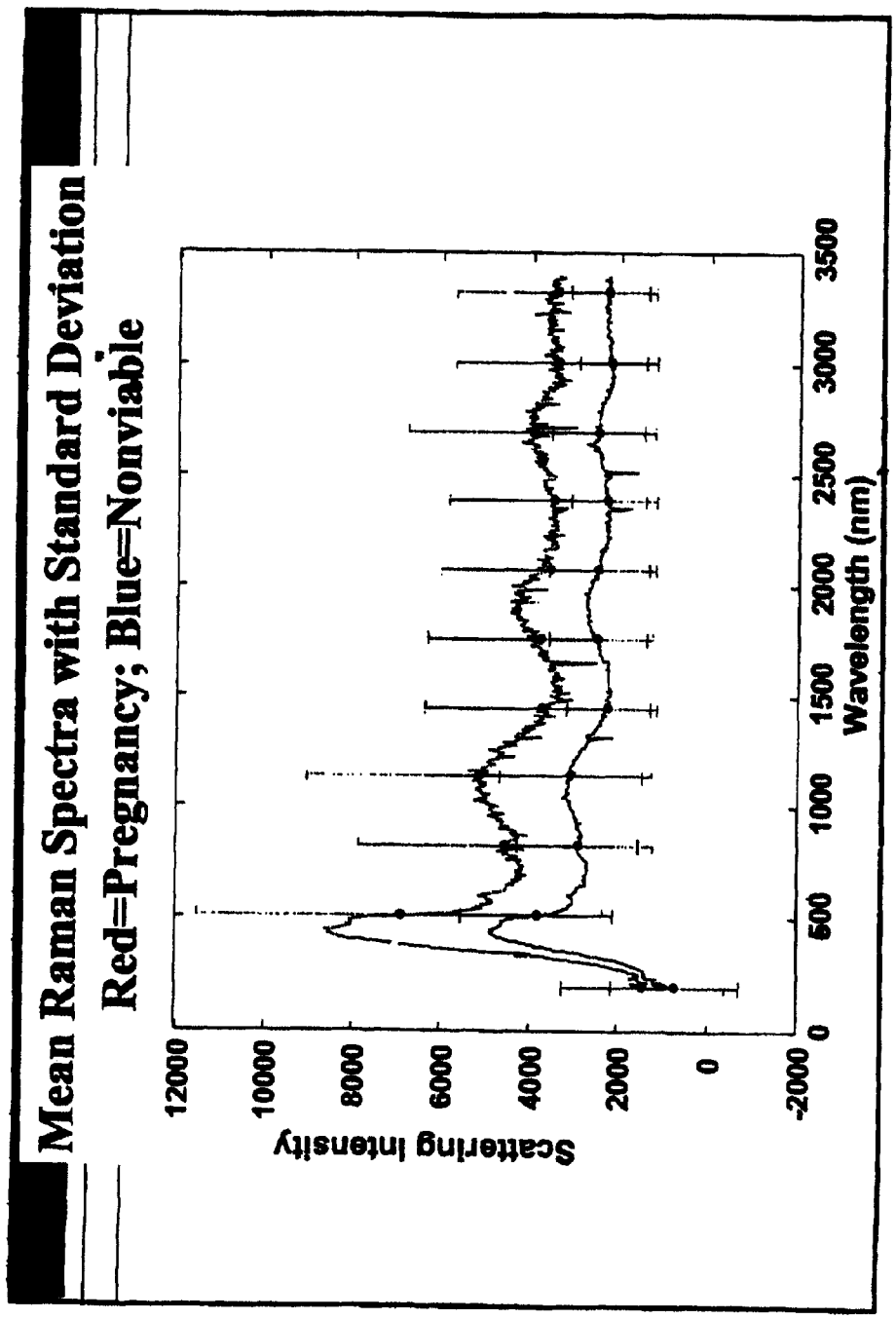
FIG. 4 shows mean Raman spectra with Standard Deviation.
Figure 5:
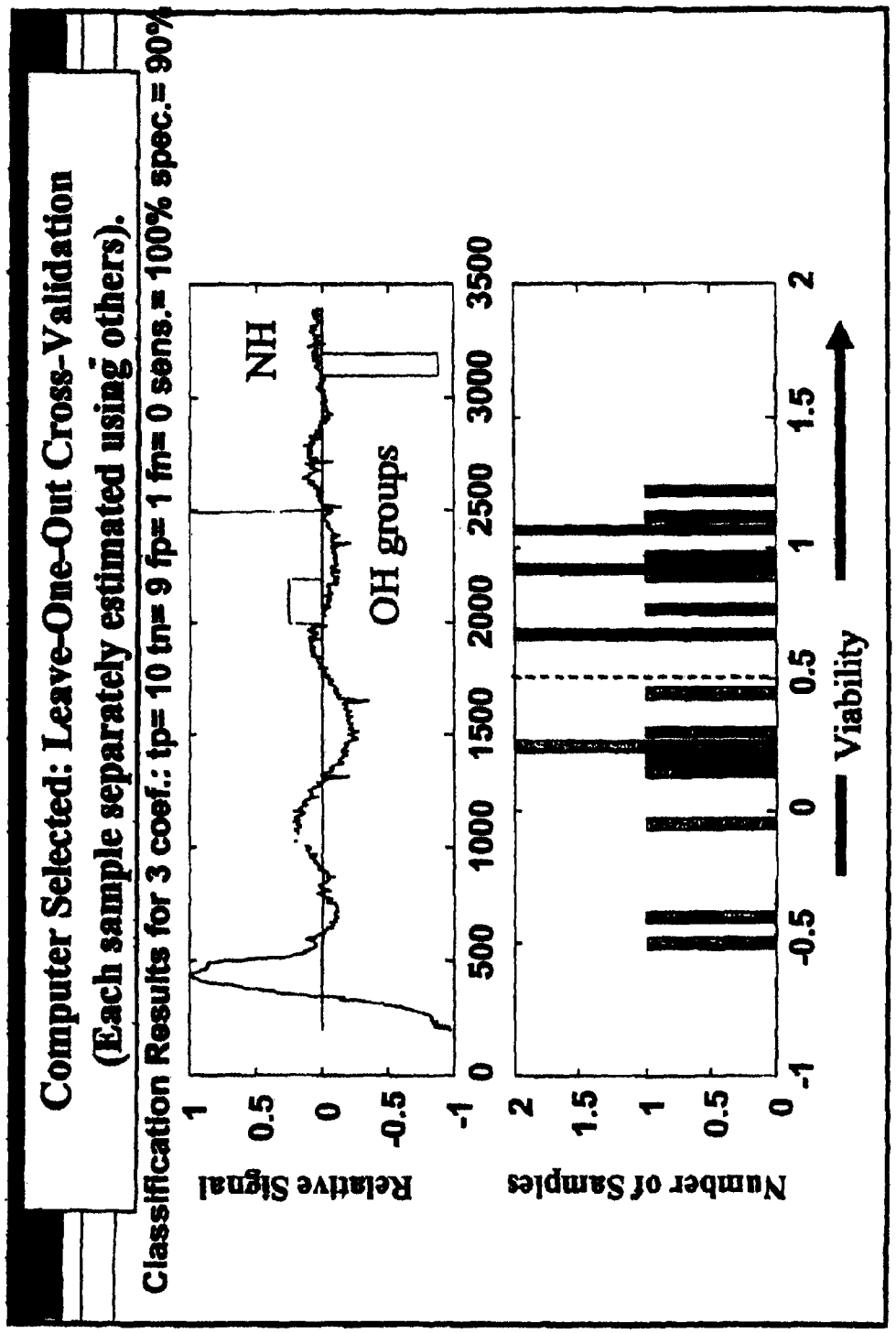
FIG. 5 shows spectra for viable samples.
Figure 6:
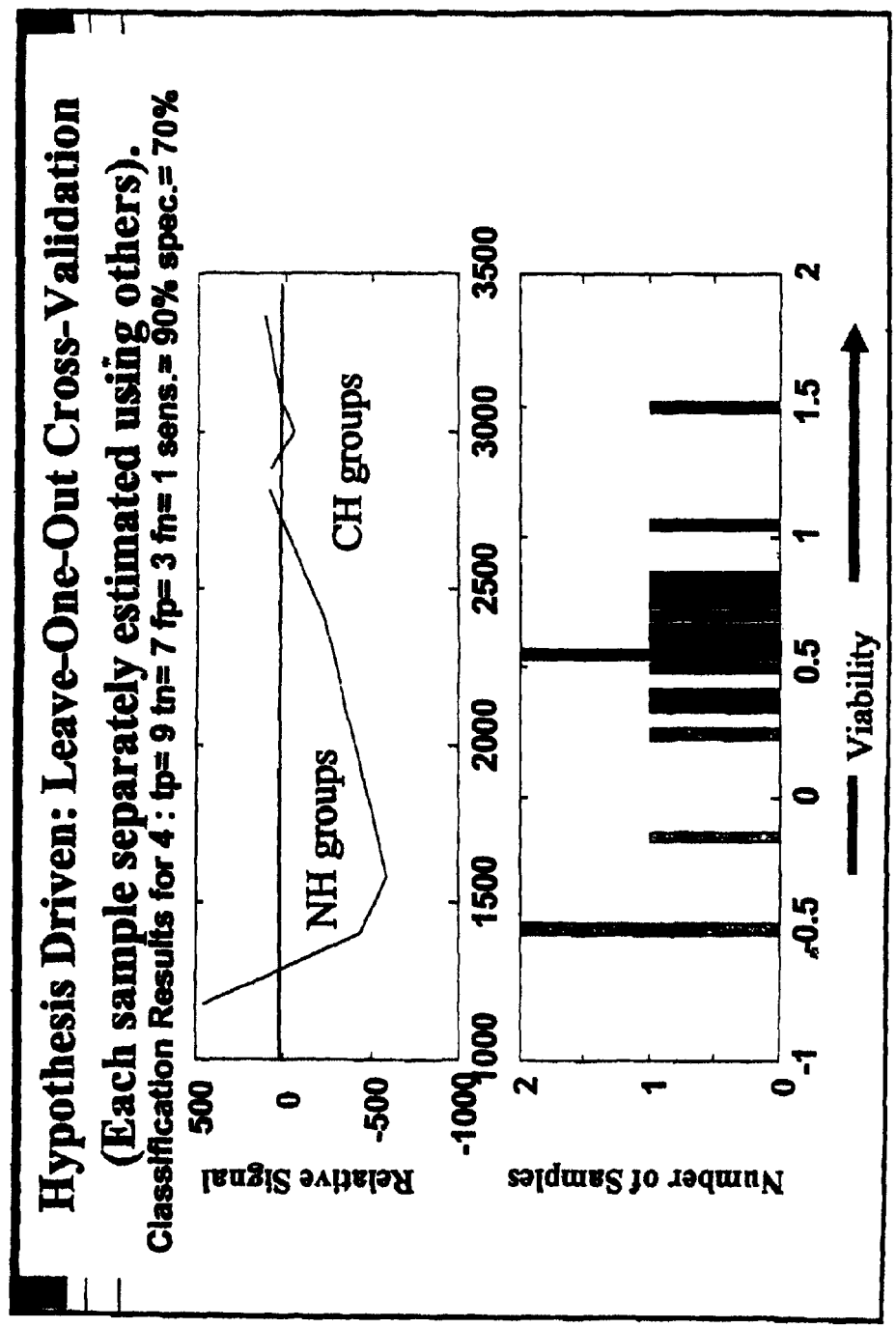
FIG. 6 shows cross validation.

The SWNIR spectra contains absorptions from a variety of molecular species. To select for major molecular species present in blood plasma, wavelength regions (15 nm width) associated with Heme (700 nm), CH (830 nm), ROH(940 nm), H2O(960 nm), OH(980 nm) and NH (1020 nm) moieties were identified as shown in FIG. 2. The integrated absorptions from these six regions were then used in the regression model described below.

Haar Wavelet Transform

The Haar transform (HT) is the oldest and simplest wavelet transform. Similarly to the Fourier transform, it projects data—for example a NIR spectrum—onto a given basis set. Unlike the Fourier transform, which uses sine and cosine functions as a basis set, the HT uses Haar wavelets. In this study, a discrete wavelet transform (DWT) was chosen over a continuous wavelet transform or a wavelet packet transform to maximize the simplicity and speed of calculations. For data defined over the range $0 < x < 1$, the family of Haar wavelets for a DWT is given by:

$$\phi(x) = \begin{cases} 1 & \text{if } 0 \leq x < 1 \\ 0 & \text{otherwise} \end{cases} \quad (1)$$

$$\psi(x) = \begin{cases} 1 & \text{if } 0 \leq x < 1/2 \\ -1 & \text{if } 1/2 \leq x < 1 \\ 0 & \text{otherwise} \end{cases} \quad (2)$$

$$\psi_{n,k}(x) = \psi(2^n x - k), \, 0 \leq k \leq 2^n - 1 \quad (3)$$

Carrying out a HT consists of decomposing a spectrum into a weighted sum of $\phi$, $\psi y$, and $\psi n,k$, where the weightings are known as "wavelet coefficients". To obtain the coefficient of the father wavelet, $\phi$, the signal over the entire data window is integrated. The weighting of the mother wavelet, $\psi$, is obtained by integrating the first half of the data points, and subtracting the sum of the second half of the data. Daughter wavelets are scaled down and translated versions of the mother wavelet. In the notation $\psi n,k$, represents the scaling, and k indicates translation. Thus, ever smaller regions in the data are summed to find the coefficients of the daughter wavelets, down to the minimum element size of the data. Daughter wavelets therefore behave like high-pass filters, while the father wavelet functions as a low-pass filter. Overall, the number of wavelet coefficients obtained is the same as the number of points in the original data set.

From the above description, it becomes apparent that Haar wavelets are simple structures, since they only have three distinct levels: +1, −1 or 0. It is however possible to simplify them even further by introducing scaled down and shifted versions of the father wavelet called scaling functions or "son" wavelets:

$$\phi_{n,k}(x) = \phi(2^n x - k), \, 0 \leq k \leq 2^n - 1 \text{ and } 0 \leq x < 1 \quad (4)$$

The mother wavelet can then be rewritten as $$\psi = \phi_{1,0} - \phi_{1,1}$$

A "son" HT can therefore be carried out on a spectrum with z points using 2z−1 wavelets that are constructed only of ones and zeros. The basis set for this wavelet transform is not orthogonal, since higher generation son wavelets are subsets of lower generations. However, son wavelets have the advantage of being monodirectional, i.e., they only go positive. Thus, unlike daughter wavelets, son wavelets do not inherently carry out a first derivative in the data processing.

In the context of spectral analysis, the HT is particularly well suited. Wavelet coefficients obtained contain both frequency and wavelength information (where "frequency" is not used in the usual sense, but refers to whether wavelets describe small- and large-scale features). Due to the retention of wavelength information, it is easier to understand the spectral meaning of HT results than FT results. Furthermore, it becomes possible to not only investigate the importance of separate wavelengths, but also spectral features of different sizes. One common application of this property is to smooth data by deleting high frequency wavelet coefficients. Alternately, large trends in data sets such as sloping baselines can be corrected by removing low frequency wavelets.

Another important trait of the HT is its ability to compress a large amount of information into a very small number of variables. Daughter wavelets are efficient in data compression, and this property is exploited in the present study to find the most parsimonious model to estimate sample properties. In comparison, the son HT does not perform as well for data compression since it is partially redundant, but it allows complete decoupling of adjacent wavelengths. Therefore this basis set should allow more freedom in feature selection. Furthermore, models built with son wavelets are easier to interpret. Since $\phi n,k$ have only two discrete levels, either a wavelength region is chosen or not chosen by the optimization algorithm. Based on the selected son wavelets, it should be possible to build a simplified instrument that uses slits or filters for sample analysis.

Both the daughter and son HT were calculated using programs written in Matlab (The Mathworks Inc., Natick, Mass.). For the daughter HT, a fast HT program based on Mallat's pyramid algorithm determined the wavelet coefficients by carrying out a series of recursive sums and differences. For the son HT, simple sums were used. Since the algorithms required the length of input data to be a power of 2, experimental spectra were padded with the last data value to reach the nearest 2n. Wavelet coefficients were determined and ordered from wide to more compact wavelets ($\phi$, $\psi$, $\psi 1,0, \ldots, \psi n,k$ or $\phi, \phi 1,0, \ldots, \phi n,k$).

Genetic Algorithm

The most parsimonious subset of variables (either wavelengths from method 1 or wavelets from method 2) to estimate a class of interest was determined by inverse least-squares (ILS) regression. When few wavelengths were involved, as in method 1, all possible combinations were modeled. When many wavelets were included in the classification (i.e. method 2), a genetic algorithm (GA) optimization to determine the best choice of wavelets was used. Using principles such as mating, crossover and mutation, many models were evaluated. For each variable combination, sample class were estimated according to $$Y = \alpha_0 + \alpha_1 X_1 + \alpha_2 X_2 + \ldots + \alpha_n X_n \quad (6)$$

where Y is the dependent variable (neurological class, i.e. 0-normal, 1-AD), $X_1, X_2, \ldots, X_n$ are independent variables (i.e. intensity of a given wavelength or wavelet coefficients), and $\alpha_0, \alpha_1, \ldots, \alpha_n$ are the coefficients determined from a set of calibration X's. Complete descriptions of GA optimization have previously been given elsewhere therefore only an overview of the method will be given here.

The best fit (optimal) models containing 1 to 15 variables were sought using the GA method. A population of individuals (i.e., models) was created by encoding chosen variables in binary and lexicographically stacking them. For preprocessed spectra of $2^n$ variables, the binary encoding used n bits. Population size was set to 1000. Every individual was used with a calibration set to build a model according to Equation 6. Computation of the corresponding standard error of calibration (SEC) was based on a test set. The two fittest individuals were identified based on their SEC, and kept for the next generation without mutation. The rest of the new population was filled by randomly mating individuals with a crossover probability of 1 and a mutation rate of 0.02. After following the population through 2000 generations, the algorithm converged to a stable solution.

The same search was carried out for models constructed with 1 to 15 variables, and their SEC were used to obtain a prediction residual error sum of squares (PRESS) plot. Let h designate the number of wavelets in the model with the minimum PRESS value. The most parsimonious model was the one with the fewest number of wavelets such that the PRESS for that model was not significantly greater than PRESS for the model with h wavelets (f-test, 99% confidence level).

Class values estimated were either 0 or 1. However, the regression above determined continuous real values. Class separation was determined using values greater that 0.5 as being from class 1 and values less than 0.5 from class 0. For each model, the sensitivity and specificity were determined and used as the criterion for model selection.

It will be appreciated that the present invention can work well with wavelengths from optical spectra in a variety of ranges, such as the NIR, SWNIR and THz ranges, as would be apparent to a person skilled in the art. In addition to absorption spectra, Raman spectra and fluorescence spectra can also be similarly analyzed. In the case of NMR, the analysis technique would be modified, as would be apparent to a person skilled in the art, to identify the desired oxidative stress components and/or perform the correlation with the desired disease or condition.

It will also be appreciated that the present invention can be used to correlate spectra to a disease or condition state, in addition to providing one or more values of oxidative stress. In the latter case, the present invention provides that a processor can generate a value representing a weighted average of a plurality of values for oxidative stress components, such that the weighted average provides a value indicative of a degree of oxidative stress of the patient.

Example 2

The exemplary methods of Example 1 may be employed in IVF procedures, and in monitoring fetal-maternal health. The methods are also applicable to harvesting oocytes, sperm, and embryos, as well as the cryopreservation of same. In vitro fertilization programs employing these methods are also contemplated.

Example 3

Figure 7:
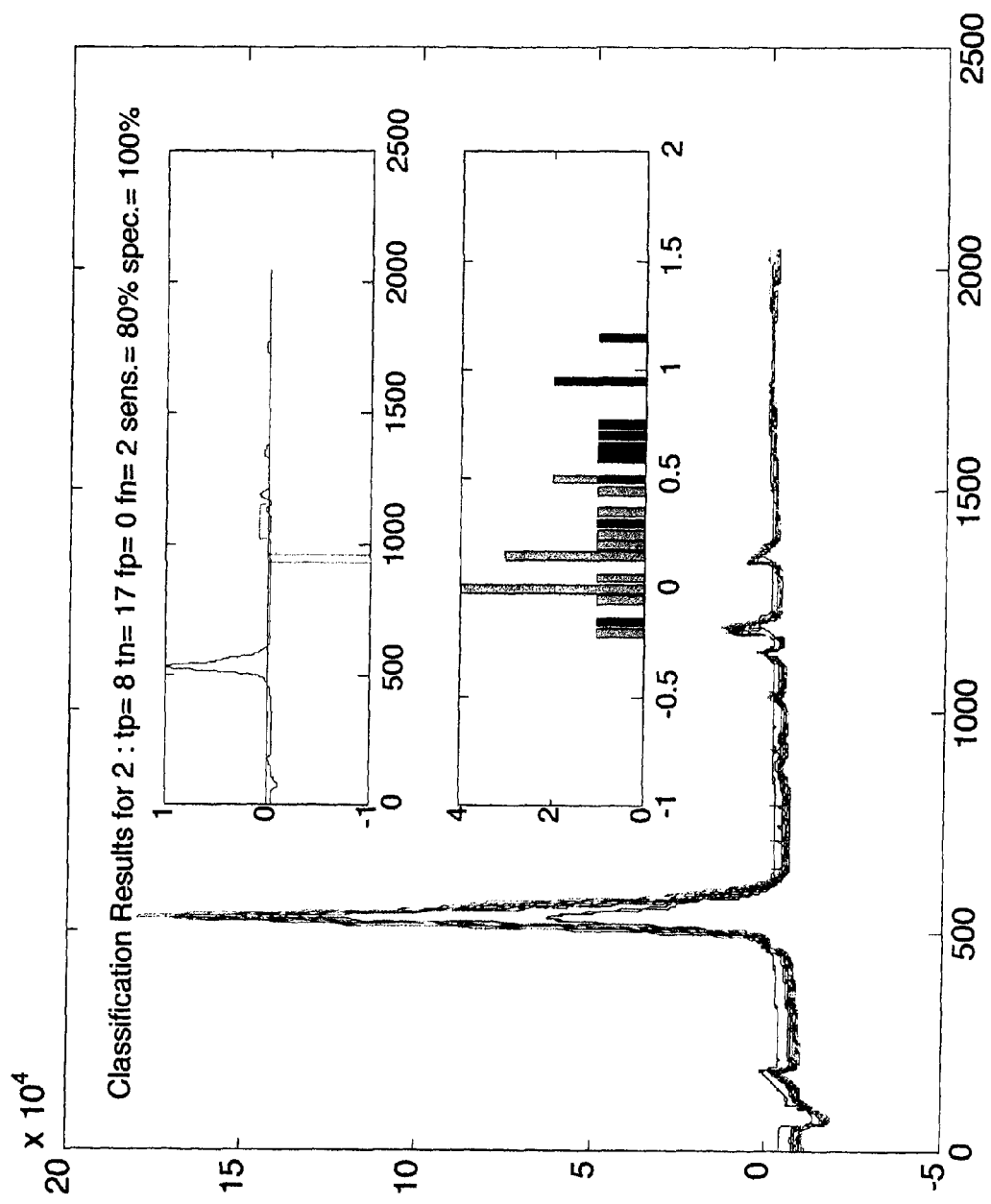
FIG. 7 is a graph of metabolomic signatures of the oxidative stress constituents in the developing embryo obtained using capillary electrophoresis with ultraviolet optical detection which identifies nutrient and metabolite fractions of the media.

Metabolomic signatures of the oxidative stress constituents in the developing embryo are also obtained using analytical separation techniques which identify nutrient and metabolite fractions of the media. An example of a separation using capillary electrophoresis with ultraviolet optical detection is given in FIG. 7. Constituents associated with embryo development are identified and have both positive and negative correlations with embryo viability. In particular, one nutrient fraction at 900 seconds is negatively correlated with embryo viability while two metabolite fractions (1000-1100 sec) are positively correlated. Combining the information from the both constituent groups, separation of embryos which result in pregnancy and those which did not, is achieved with a sensitivity of 80% and a specificity of 100%. Using the same methodology developed here, separations techniques such as, other electromotive separation techniques, liquid and gas chromatography, can also be used for separation of these metabolomic signatures from developing cells to viability assessment.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth, and as follows in the scope of the appended claims.

REFERENCES

Sies, H., Oxidative Stress. Oxidants and Antioxidants. 1991, New York: Elsevier. 507.
Hailiwell, B. and J. M. C. Gutteridge, Free Radicals in Biology and Medicine. 3 ed. 1999, Oxford: Oxford University Press Inc. 736.
Albuszies, G. and U. B. Bruckner, Antioxidant therapy in sepsis. Intensive Care Med, 2003.29(10): p. 1632-6.
Abu-Zidan, F. M., L. D. Plank, and J. A. Windsor, Proteolysis in severe sepsis is related to oxidation of plasma protein. Eur J Surg, 2002. 168(2): p. 19-23.
C. E. W. Gributs, D. H. Bums, Applied Optics, 2003, 42116. p. 2923-2930
M. J. McShane, B. D. Cameron, G. L. Cote, C. H. Spiegelman, Applied Spectroscopy 1999, 53, p. 1575-1581
Alikani, M, Calderon G, Tornkin G, Garrisi J, Kokott M, Cohen J. Cleavage anomalies in early human embryos and survival after prolonged culture in vitro. Hum. Reprod. 2000; 152634-43.
Almagor M, Bejar C, Kafka I, Yaffe H. Pregnancy rates after the communal growth of preimplantation embryos in vitro. Fertil Steril 1996; 66:394-97.
Balaban B, Urman B, Isiklar A, Alatas C, Aksoy S, Mercan R, et al. The effect of pronuclear morphology on embryo quality parameters and blastocyst transfer outcome. Hum Reprod 2001; 16:2357-6 1.
Blake D, Proctor M, Johnson N, Olive D. Cleavage stage versus blastocyst stage embryo transfer in assisted reproduction (Cochrane Review). Cochrane Database Syst Rev 2002; (2):CD002 118.
Bos-Miluch A. Mattos A L, Ferrari A N. Early cleavage of human embryos: an effective method for predicting successful IVF/ICSI outcome. Hum Reprod 2001; 16:2658-6 1.
Fenwick J, Platteau P, Murdoch A P, Herbert M. Time from insemination to first cleavage predicts developmental competence of human preimplantation embryos in vitro. Hum Reprod 2002; 17:407-12.
Fisch J D, Rodriguez H, Ross R, Overby G, Sher G. The Graduated Embryo Score (GES) predicts blastocyst formation and pregnancy rate from cleavage-stage embryos. Hum Reprod 2001; 16: 1970-5.
Foumel S, Huc X, Aguerre-Gin M, Solier C, Legros M, Proud-Brethenou C, Moussa M, Chaouat G, Berrebi A, Bensussan A, Lenfant F, Le Bbouteiller P: Comparative reactivity of different HLA-G monoclonal antibodies to soluble HLA-G molecules. Tissue Antigens 55:510, 2000.
Fuzzi B, Rizzo R, Criscuoli L, Noci I, Melchiom L, Scarselli B, Bencini E, Menicucci A, Baricordi O: HLA-G expression in early embryos is a fundamental prerequisite for the obtainment of pregnancy. Eur J Lmmunol 32:3 11, 2002.
Gardner D K, Phil D, Vella P, Lane M, Wagley L, Schlenker T, Schoolcraft W. Culture and transfer of human blastocysts increases implantation rates and reduces the need for multiple embryo transfers. Fertil Steril 1998; 69:84-8.
Gianaroli L, Magli M C. Fenaretti A P, Fiorentino A, Garrisi J, Munne S.; Preimplantation genetic diagnosis increases the implantation rate in human in vitro fertilization by avoiding the transfer of chromosomally abnormal embryos. Fenil Steril 1997; 68; 1128-3 1.
Hunt J S: HLA and maternal-fetal relationship. Austin, Tex. RG Landes Co, 1996.
Le Bouteiller P, Blaschitz A: The functionality of HLA-G is emerging. Immunol Rev 1999.
Levron J, Shulman A, Bider D, Seidman D, Levin T, Dor J. A prospective randomized study comparing day 3 with blastocyst-stage embryo transfer. Fertil Steril 2002; 77: 1300-01.
Loke Y W, King A: Human Implantation: Cell Biology and Immunlogy. Cambridge, Cambridge University Press, 1995.
Lonergan P, Khatir H, Piurni F, Rieger D. Humblot P, Boland M P. Effect of time interval from insemination to first cleavage on developmental characteristics, sex ratio and pregnancy rate after transfer of bovine embryos. J Reprod Fertil 1999; 117: 159-67.
Ludwig M, Schopper B, Al-Hasano S, Diedrich K. Clinical use of a pronuclear stage score following intracytoplasmic sperm injection: impact on pregnancy rates under the conditions of the German embryo protection law. Hum Reprod 2000; 15:325-9.
Lundin K, Bergh C, Hardarson T. Early embryo cleavage is a stron indicator of embryo quality in human VF. Hum Reprod 2001; 16:2652-7.
Magali M C, Jones G M. Gras L, Gianaroli L, Korman I, Trounson A. Chromosome mosaicism in day 3 aneuploid embryos that develop to morphologically normal blastocysts in vitro. Hum Reprod 2000; 15: 178 1-86.
McMaster M, Zhou Y, Shorter S, Kapasi K, Geraghty D, Lim K; Fisher S: HLA-G isoforms produced by placental cytotrophoblast and found in amniotic fluid are due to unusual glycosilation. J Immunol 160:5922, 1998.
Menicucci A, Noci I, Fuzzi B, Criscuoli L, Baricordi O, Mattiuz P I: Non-classic sHLA class I in human oocyte culture medium. Hum Immuno, I60: 1057, 1999.
Milki A A, Hinckley M D, Gebhart J, Dasig D, Westphal L, Behr B. Accuracy of day 3 criteria for selecting the best embryos. Fertil Steril 2002; 77: 1191-5.
Milki A A, Hinckley M D, Fisch J D, Dasig D, Behr B. Comparison of Day 3-ET to Blastocyst-ET in a Similar Patient Population: Fertil Steril 2000; 73(1): 126-9.
Milki A A, Fisch J D, Behr B.; Two blastocyst transfer has similar pregnancy rates and a decreased multiple gestation rate compared to three blastocyst transfer. Fertil Steril 1999; 72:225-8.
Puissant F, Van Rysselberge M, Barlow P, Deweze J, Leroy F. Embryo scoring as a prognostic tool in IVF treatment. Hum Reprod 1987; 2:705-8.
Rijnders P M, Jansen C A. The predictive value of day 3 embryo morphology regarding blastocyst formation, pregnancy and implantation rate after day 5 transfer following in vitro fertilization or intracytoplasmic sperm injection. Hum Reprod 1998; 13:2869-73.

Shoukir Y, Carnpana A, Farley T, Sakkas D. Early cleavage of in vitro fertilized human embryos to the 2-cell stage: a novel indicator of embryo quality and viability. Hum Reprod 1997; 12: 153 1-6.

Scott L A, Smith S. The successful use of pronuclear embryo transfers the day following oocyte retrieval. Hum Reprod 1998; 13: 1003-13.

Scott L. Alvero R. Leondires M, Miller B. The morphology of human pronuclear embryos is positively related to biastocyst development and implantation. Hum Reprod 2000; 15:2394-403.

Spyropoulou I, Kararnalegos C, Bolton V N. A prospective randomized study comparing the outcome of in vitro fertilization and embryo transfer following culture of human embryos individually or in groups before embryo transfer on day 2. Hum Reprod 1999; 14:76-9.

Tesarik J, Junca A M, Hazout A, Aubriot F X, Nathan C, Cohen-Bacrie P, Dumont-Hassan M. Embryos with high implantation potential after intracytoplasmic sperm injection can be recognized by a simple, non-invasive examination of pronuclear morphology. Hum Reprod 2000; 15: 1396-99.

Tsai Y C, Chung M T, Sung Y H, Tsai F, Tsai Y T, Lin L Y. Clinical value of early cleavage embryo. Int J Gynaecol Obstet 2002; 76:293-7.

Van Lierop M, Wijnands F, Loke Y, Emmer P, Lukassen H, Braat D, Van der Meer A, Mosselman S, Josten I: Detection of HLA-G by specific sandwich ELISA using monoclonal antibodies G233 and 56B. Mol Hum Reprod 776, Aug. 20, 2002.

Ziebe S, Petersen K, Lindenberg S, Andersen A G, Gabrielsen A, Andersen A N. Embryo morphology or cleavage stage: how to select the best embryos for transfer after in vitro fertilization. Hum Reprod 1997; 12: 1545-9.

Zollner U, Zollner K P, Hartl G, Diet1 J, Steck T. The use of a detailed zygote score after NF/ICSI to obtain good quality blastocysts: the German experience. Hum Reprod. 2002; 17: 1327-33.

The invention claimed is:

1. An apparatus for controlling culture of one or more cells growing in vitro and exchanging metabolites with a culture medium, the apparatus comprising:
    a spectral acquisition device for acquiring a spectrum of said culture medium;
    a database of correlation data relating spectral data of said culture medium to a state of said cells exchanging metabolites with said culture medium;
    a state determination processor generating data representing said state using said correlation data and said spectrum;
    a culture medium controller generating control signals for effecting an adjustment in said culture medium in response to said data representing said state.

2. The apparatus of claim 1, wherein said adjustment is effected external to said culture medium.

3. The apparatus of claim 1, wherein said adjustment is an adjustment in ambient temperature or gas composition.

4. The apparatus of claim 1, wherein said adjustment is an addition of a substance to said culture medium.

5. The apparatus of claim 1, wherein said adjustment is a substitution of said culture medium.

6. The apparatus of claim 1, wherein said spectrum contains information regarding oxidative stress of at least one component of said culture medium.

7. The apparatus of claim 6, wherein said spectral acquisition device is optical.

8. The apparatus of claim 7, wherein said spectral acquisition device operates in the near infrared range.

9. The apparatus of claim 1, wherein said state is viability of said cells exchanging metabolites with the culture medium.

10. The apparatus of claim 1, wherein said one or more cells are oocytes, embryos, sperm or stem cells.

\* \* \* \* \*